(12) United States Patent
Min et al.

(10) Patent No.: US 11,779,769 B2
(45) Date of Patent: Oct. 10, 2023

(54) METHOD AND DEVICE FOR AVOIDING ATRIAL ACTIVITY OVERSENSING ON HIS SENSING CHANNEL

(71) Applicant: Pacesetter, Inc., Sylmar, CA (US)

(72) Inventors: Xiaoyi Min, Ventura, CA (US); Wenwen Li, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 318 days.

(21) Appl. No.: 16/988,866

(22) Filed: Aug. 10, 2020

(65) Prior Publication Data

US 2021/0085970 A1  Mar. 25, 2021

Related U.S. Application Data

(60) Provisional application No. 62/902,698, filed on Sep. 19, 2019.

(51) Int. Cl.
*A61N 1/365* (2006.01)

(52) U.S. Cl.
CPC .................. *A61N 1/365* (2013.01)

(58) Field of Classification Search
CPC ..................................... A61N 1/365
USPC ........................................... 607/25
See application file for complete search history.

(56) References Cited

U.S. PATENT DOCUMENTS

| 6,718,206 B2 | 4/2004 | Casavant |
| 8,565,880 B2 | 10/2013 | Dong et al. |
| 8,942,805 B2 | 1/2015 | Shuros et al. |
| 2019/0134404 A1* | 5/2019 | Sheldon ............. A61N 1/37247 |
| 2020/0353266 A1* | 11/2020 | Min .................... A61N 1/36521 |
| 2021/0393967 A1* | 12/2021 | Min ....................... A61N 1/371 |

OTHER PUBLICATIONS

Burri et al. "Device Programming for His Bundle Pacing" Circulation Arrhythmia Electrophysiology; Feb. 2019, 11 pages.
Padeletti et al. "Simultaneous His Bundle and Left Ventricular Pacing for Optimal Cardiac Resynchronization Therapy Delivery Acute Hemodynamic Assessment by Pressure-Volume Loops" Circulation Arrhythmia Electrophysiology; 2016; 8 pages.
(Continued)

*Primary Examiner* — Nicole F Lavert
(74) *Attorney, Agent, or Firm* — THE SMALL PATENT LAW GROUP LLC; Dean D. Small

(57) ABSTRACT

Methods and systems are provided herein for pacing a HIS bundle of a patient heart using an implantable medical device (IMD). The methods and systems obtain cardiac activity (CA) signals over a HIS sensing channel, the HIS sensing channel utilizing a HIS electrode; identify at least one of a P-wave duration (PWD), an intrinsic atrial-HIS (AH) delay, or an intrinsic atrial conduction delay (IACD); calculate an atrial oversensing avoidance (AOA) window based on at least one of the PWD, AH delay or IACD; analyze the CA signals, obtained over the HIS sensing channel during the AOA window, for an atrial activity (AA) component; based on the analyzing operation, adjust a ventricular event (VE) sensitivity profile utilized by the HIS sensing channel; monitor the CA signals, obtained over the HIS sensing channel during an alert window based on the VE sensitivity profile, for a ventricular component indicative of a ventricular event; and manage HIS bundle pacing based on the ventricular event.

24 Claims, 17 Drawing Sheets

(56) References Cited

OTHER PUBLICATIONS

Min et al. "Comparison of P Wave Durations as Assessed with the Bipolar and Unipolar Atrial Intracardiac Electrograms: Applicability to QuickOpt™" Computers in Cardiology; 2007; 4 pages.

* cited by examiner

METHOD AND DEVICE FOR AVOIDING ATRIAL ACTIVITY OVERSENSING ON HIS SENSING CHANNEL

REFERENCE TO RELATED APPLICATIONS

The present application claims priority to U.S. Provisional Application No. 62/902,698, Titled "METHOD AND DEVICE FOR AVOIDING ATRIAL ACTIVITY OVERSENSING ON HIS SENSING CHANNEL" which was filed on 19 Sep. 2019, the complete subject matter of which is expressly incorporated herein by reference in its entirety.

BACKGROUND

Embodiments of the present disclosure generally relate to HIS bundle pacing and more specifically, to managing HIS sensing operations to avoid atrial activity over sensing.

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of HIS (also referred to as the HIS bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pace-making and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation devices are intended to fill in when the natural pacing functionality of the patient's heart falls or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the HIS bundle are intact and disruption of ventricular rhythm is the result of conduction disorders residing in the left and/or right bundle branches. Dilatation of the heart due to congestive heart failure (CNF) has been associated with delayed conduction through the ventricles. This delayed conduction leads to reduced hemodynamic efficiency of the failing heart because of the resulting poor synchronization of the heart chambers.

Direct stimulation of the HIS bundle has been found to provide hemodynamic improvement for various patients including those suffering from dilated cardiomyopathy but having normal ventricular activation. Other examples of patients that may benefit from direct stimulation of the HIS bundle include those with atrioventricular junction (AVJ) ablation or third-degree AV block that require permanent ventricular pacing. Accordingly, the natural conduction system, when intact, can provide hemodynamically optimal depolarization timing of the heart chambers.

However, an opportunity remains to improve upon HIS bundle pacing methods and systems. For example, IMDs that include a HIS bundle pacing (HBP) lead also have a HIS bundle sensing channel that utilizes one or more electrodes on the HIS bundle pacing lead to sense atrial and ventricular activity. Systems, that utilize HIS bundle pacing, experience oversensing of atrial signals over the HIS sensing channel. Heretofore, clinicians have attempted to avoid over sensing by manually programming parameters associated with the HIS sensing channel, such as to lower sensitivity and to extend a ventricular blanking period.

However, not all patients are the same and individual patient's experience variations in cardiac behavior. Accordingly, manually setting the foregoing parameters does not always achieve a desired result. In current devices, the ventricular refractory period (VRP) begins upon detection of a ventricular paced (Vp) event or intrinsic ventricular sensed (Vs) event. The length of the VRP is set to prevent oversensing T waves and wide QRS complexes. With HBP, there is a longer delay from a HIS paced (Hp) event to a ventricular sensed (Vs) event (e.g., 30 ms-60 ms) with selective capture. However, the longer delay is not currently included in the VRP. Also, in current systems, a clinician programs the ventricular blanking period (VBP) to include a peak of an Ap event. However, the clinician programmed VRP and VBP do not avoid oversensing of atrial activity in many situations. When the HIS lead is implanted in the RA, the HIS sensing channel will detect near field (NF) atrial signals and far field (FF) ventricular signals, both of which may have comparable amplitudes in some cases. When the NF atrial signal and FF ventricular signal have similar amplitudes, the IMD experiences a challenge in attempting to deal through sensitivity settings and refractory period lengths.

A need remains for methods and devices that overcome the foregoing and other disadvantages of conventional approaches.

SUMMARY

In accordance with embodiments herein, a method is provided for pacing a HIS bundle of a patient heart using an implantable medical device (IMD), the method comprising: obtaining cardiac activity (CA) signals over a HIS sensing channel, the HIS sensing channel utilizing a HIS electrode; identifying at least one of a P-wave duration (PWD), an intrinsic atrial-HIS (AH) delay, or an intrinsic atrial conduction delay (IACD); calculating an atrial oversensing avoidance (AOA) window based on at least one of the PWD, AH delay or IACD; analyzing the CA signals, obtained over the HIS sensing channel during the AOA window, for an atrial activity (AA) component; based on the analyzing operation, adjusting a ventricular event (VE) sensitivity profile utilized by the HIS sensing channel; monitoring the CA signals, obtained over the HIS sensing channel during an alert window based on the VE sensitivity profile, for a ventricular component indicative of a ventricular event; and managing HIS bundle pacing based on the ventricular event.

Optionally, the calculating operation further comprises setting the AOA window to equal at least one of: the PWD when a difference between the AH delay and the PWD is greater than or equal to an alert minimum threshold; or a percentage of the PWD. Optionally, the method further comprises obtaining a second group of the CA signals over a right atrial (RA) sensing channel, a left ventricular (LV) sensing channel and/or electrocardiogram (ECG) sensing channel, the identifying including identifying at least one of the PWD or IACD based on the second group of the CA signals. Optionally, the adjusting operation lowers a sensitivity level of the VE sensitivity profile for the HIS sensing channel. Optionally, the method further comprises maintaining a count of a number of AA components over a series of beats and, based on the count, determining whether to maintain or change current settings for the length of the AOA window and/or sensitivity profile. Optionally, the AOA window represents a time window enclosing atrial component activity components. Optionally, the calculating operation calculates a first AOA window, the method further comprising providing a second AOA window, that extends continuous with the first AOA window, the analyzing operation further comprising analyzing the CA signals during the first and second AOA windows.

Optionally, the first and second AOA windows have at least one of different durations or sensitivities. Optionally, the analyzing operation is performed over a number of cardiac beats, from which one or more characteristics of interest from the AA component are mathematically combine and utilized to adjust the VE sensitivity profile. Optionally, the analyzing operation is performed in a beat or a few beats over one or more respiration cycles in one channel connected to the HIS lead, from which comparisons to programming settings of the VE sensitivity profile in the other channel(s) also connected to the HIS lead for HIS pacing and the VE sensitivity profile adjustments when criteria are met. Optionally, the analyzing operation is performed in one beat, from which comparisons to programming settings of the VE sensitivity profile in the other channel(s) also connected to the HIS lead for HIS pacing to decide adjustments when criteria are met. Optionally, the method further comprises defining a post atrial ventricular period (PAVP) window, identifying peaks in the CA signal that exceed a PAVP sensitivity threshold utilized during the PAVP window, and defining a length of the AOA window based on a timing of a last one of the peaks in the CA signals during the PAVP window that exceed the PAVP sensitivity threshold.

In accordance with embodiments herein, a system is provided that comprises: a HIS electrode configured to be located proximate to the HIS bundle and to at least partially define a HIS sensing channel; memory to store cardiac activity (CA) signals obtained over the HIS sensing channel, the memory to store program instructions; and one or more processors that, when executing the program instructions, are configured for: identifying at least one of a P-wave duration (PWD), an intrinsic atrial-HIS (AH) delay, or an intrinsic atrial conduction delay (IACD); calculating an atrial oversensing avoidance (AOA) window based on at least one of the PWD, AH delay, or IACD; analyzing the CA signals, obtained over the HIS sensing channel during the AOA window, for an atrial activity (AA) component; based on the analyzing operation, adjusting a ventricular event (VE) sensitivity profile utilized by the HIS sensing channel; monitoring the CA signals, obtained over the HIS sensing channel during an alert window based on the VE sensitivity profile, for a ventricular component indicative of a ventricular event; and managing HIS bundle pacing based on the ventricular event.

Optionally, the one or more processors are further configured to set the AOA window to equal at least one of: the PWD when a difference between the AH delay and the PWD is greater than or equal to an alert minimum threshold; or a percentage of the PWD. Optionally, the calculating operation, by the one or more processors, further comprises to set first and second AOA windows that extend continuous with one another following an atrial event, the first AOA window having a length corresponding to at least one of a predetermine time interval or a percentage of the PWD, the second AOA window having a length corresponding to at least one of a percentage of the PWD or the AICD.

Optionally, the adjusting operation lowers a sensitivity level of the VE sensitivity profile for the HIS sensing channel. Optionally, the one or more processors are further configured to maintain a count of a number of AA component over a series of beats and, based on the count, determining whether to maintain or change current settings for the length of the AOA window and/or sensitivity profile. Optionally, the AOA window represents a post atrial ventricular period (PAVP) window. Optionally, the method further comprises an implantable medical device having a housing that includes the memory and the one or more processors, the housing configured to be coupled to the RA electrode and HRIS electrode. Optionally, the method further comprising an implantable medical device (IMD) having at least a portion of the one or more processors and an external device having at least a portion of the one or more processors, the IMD and external device both performing at least a portion of the identifying, calculating, analyzing, adjusting, monitoring and managing operations.

Optionally, the one or more processors are configured to perform the analyzing operation over a number of cardiac beats, from which one or more characteristics of interest from the AA components are mathematically combine and utilized to adjust the VE sensitivity profile. Optionally, the one or more processors are further configured to define a post atrial ventricular period (PAVP) window, identify the maximum peak in the CA signal in the PAVP window, and define a length of the AOA window based on a timing of the last intercept of the CA signals during the PAVP window to a threshold set equal to or lower than the sensitivity threshold for VE in alert period or based on the peak location and PAVP window size.

DETAILED DESCRIPTION

Figure 1:
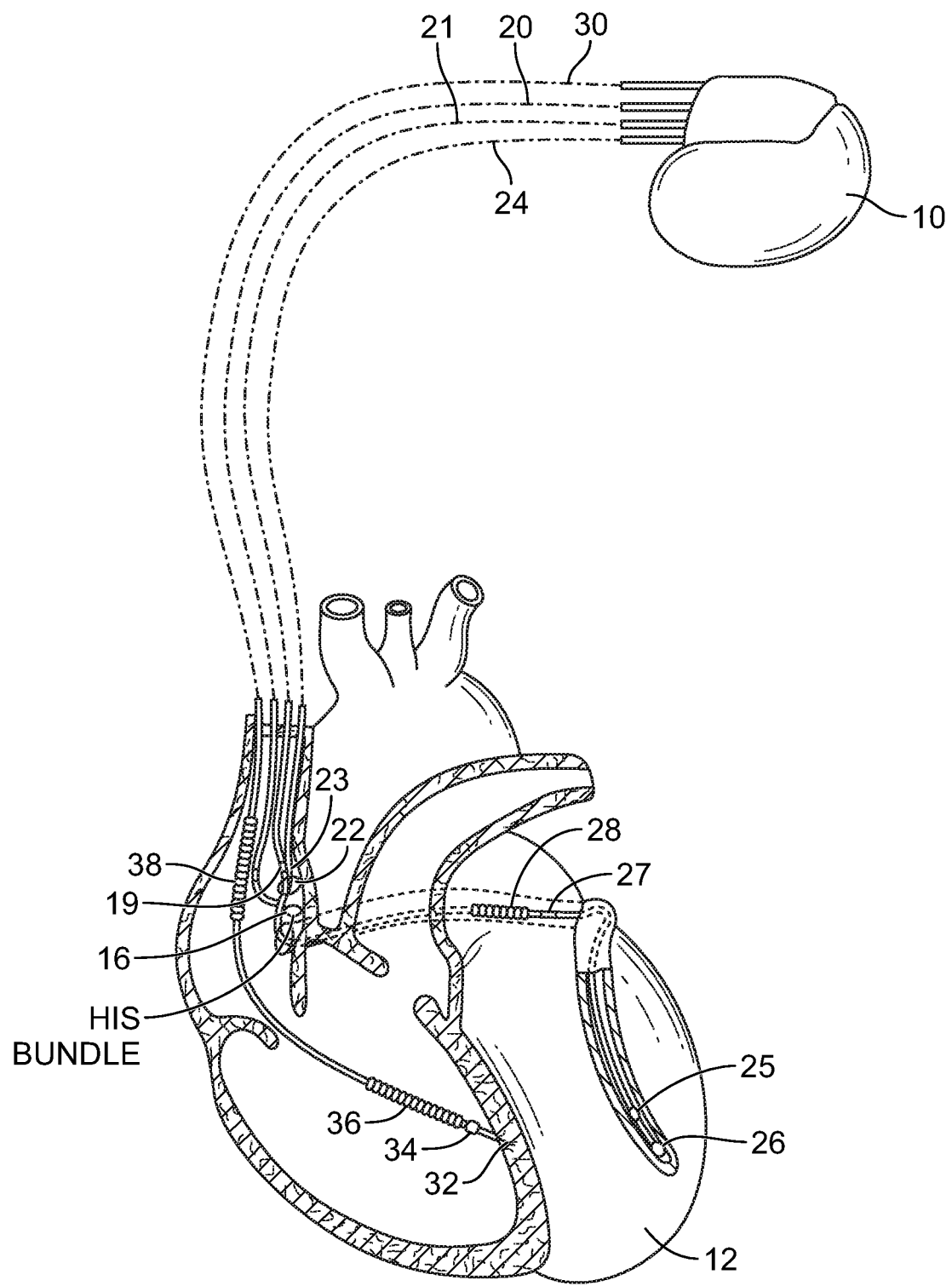
FIG. 1 illustrates a stimulation device in electrical communication with a patient's heart by way of one or more of four leads and suitable for delivering multi-chamber stimulation and shock therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. By way of example, one or more operations of each method described herein may be implemented by one or more processors or circuitry of an implantable medical device, while one or more other operations of the methods described herein may be implemented by one or more processors of an external device, such as a local external device, clinician programmer and/or a remote server. While the operations of some methods may be described as performed by the processor(s) of one device, additionally, some or all of such operations may be performed by the processor(s) of another device described herein.

The terms "atrial activity component" and "AA component" shall mean atrial pacing spikes or atrial evoked propagation or spontaneous intrinsic atrial propagation sensed at HIS lead.

The term "intrinsic atrial-HIS delay" or "intrinsic AH delay" shall mean conduction delay from the time of As or Ap event in RA channel to the time HIS signal sensed at HIS lead electrodes. Practically it can be derived from time delay of As or AP to sensed ventricular depolarization (A-Vs)–the delay from pacing HIS to V sense (HVs)+pacing latency at HIS. The peak means the max peak in the specified window with either rectified or the absolute values.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from a IMD and/or a remote server. The obtaining operation may be from the perspective of a remote server, such as when receiving the data, signals, information, etc. at a network interface from a local external device and/or directly from a the IMD. The remote server may also obtain the data, signals, information, etc. from local memory and/or from other memory, such as within a cloud storage environment and/or from the memory of a workstation or clinician external programmer.

Embodiments may be implemented in connection with one or more implantable medical devices (IMDs). Non-limiting examples of IMDs include one or more of a cardiac monitoring device, pacemaker, cardioverter, cardiac rhythm management device, defibrillator, neurostimulator, leadless monitoring device, leadless pacemaker and the like. For example, embodiments herein may be implemented by, or in connection with, the systems and methods described in U.S. Patent Application 2019/0022378, titled "SYSTEMS AND METHODS FOR AUTOMATED CAPTURE THRESHOLD TESTING AND ASSOCIATED HIS BUNDLE PACING", published Jan. 24, 2019, and issued as U.S. Pat. No. 10,981,001, and/or U.S. patent application Ser. No. 15/973,351, issued as U.S. Pat. No. 11,020,036, titled "METHOD AND SYSTEM TO DETECT R-WAVES IN CARDIAC ARRHYTHMIC PATTERNS" the complete subject matter of which is incorporated herein by reference in its entirety.

Additionally or alternatively, embodiments may be implemented in connection with a transvenous IMD and/or one or more leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "LEADLESS NEUROSTIMULATION DEVICE AND METHOD INCLUDING THE SAME", which are hereby incorporated by reference. Additionally or alternatively, the IMD may include one or more structural and/or functional aspects of the device(s) described in U.S. Pat. No. 8,391,980 "METHOD AND SYSTEM FOR IDENTIFYING A POTENTIAL LEAD FAILURE IN AN IMPLANTABLE MEDICAL DEVICE" and U.S. Pat. No. 9,232,485 "System And Method For Selectively Communicating With An Implantable Medical Device", which are hereby incorporated by reference. The LIMD may communicate with one another to practice the methods and systems described herein. Additionally or alternatively, a transvenous IMD may communicate with one or more LIMD to practice the methods and systems described herein.

Additionally or alternatively, embodiments may be implemented in connection with a transvenous or leadless IMD and a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018 and issued as U.S. Pat. No. 10,765,860; U.S. application Ser. No. 15/973,219, titled "IMPLANTABLE MEDICAL SYSTEMS AND METHODS INCLUDING PULSE GENERATORS AND LEADS" filed May 7, 2018 and issued as U.S. Pat. No. 10,722,704; U.S. application Ser. No. 15/973,249, titled "SINGLE SITE IMPLANTATION METHODS FOR MEDICAL DEVICES HAVING MULTIPLE LEADS", filed May 7, 2018 and issued as U.S. Pat. No. 11,045,643, which are hereby incorporated by reference in their entireties. Further, one or more combinations of IMDs may be utilized from the above incorporated patents and applications in accordance with embodiments herein.

Additionally or alternatively, embodiments herein may be implemented by, or in connection with, the systems and methods described in U.S. Patent Application 2019/0022378, titled "SYSTEMS AND METHODS FOR AUTOMATED CAPTURE THRESHOLD TESTING AND ASSOCIATED HIS BUNDLE PACING", published Jan. 24, 2019 and issued as U.S. Pat. No. 10,981,001, and/or U.S. patent application Ser. No. 15/973,351, titled "METHOD AND SYSTEM TO DETECT R-WAVES IN CARDIAC ARRHYTHMIC PATTERNS", issued as U.S. Pat. No. 11,020,036; U.S. application Ser. No. 16/904,837, filed Jun. 18, 2020, titled "SYSTEMS AND METHODS FOR IMPROVED HIS BUNDLE AND BACKUP PACING TIMING", published Dec. 23, 2021 as U.S. Patent Application 2021/0393967, the complete subject matter of which are incorporated herein by reference in their entireties.

Additionally or alternatively, embodiments herein may be implemented by, or in connection with, the systems and methods described in U.S. application Ser. No. 16/904,837, Titled "SYSTEMS AND METHODS FOR IMPROVED HIS BUNDLE AND BACKUP PACING TIMING", filed Jun. 18, 2020 and published Dec. 23, 2021 as U.S. Patent Application 2021/0393967; U.S. application Ser. No. 16/871,166, Titled "SYSTEMS AND METHODS FOR IMPROVED HIS BUNDLE AND BACKUP PACING TIMING", filed May 11, 2020 and published Jan. 21, 2021 as U.S. Patent Application 2021/0016097; U.S. Provisional Application 62/875,863, Titled "SYSTEMS AND METHODS FOR IMPROVED HIS BUNDLE AND BACKUP PACING TIMING", filed Jul. 18, 2019 and providing priority to aforementioned U.S. Patent Application 2021/0016097; U.S. application Ser. No. 16/181,234, Titled "AUTOMATED OPTIMIZATION OF HIS BUNDLE PACING FOR CARDIAC RESYNCHRONIZATION THERAPY", filed Nov. 5, 2018 and issued as U.S. Pat. No. 10,850,107; U.S. application Ser. No. 16/138,766, Titled "SYSTEMS AND METHODS FOR AUTOMATED CAPTURE THRESHOLD TESTING AND ASSOCIATED HIS BUNDLE PACING", filed Sep. 21, 2018 and issued as U.S. Pat. No. 11,027,136; U.S. application Ser. No. 15/653,357, Titled "SYSTEMS AND METHODS FOR AUTOMATED CAPTURE THRESHOLD TESTING AND ASSOCIATED HIS BUNDLE PACING", filed Jul. 18, 2017 and issued as U.S. Pat. No. 10,981,001; U.S. Provisional Application 62/948,047, Titled "AUTOMATIC PACING IMPULSE CALIBRATION USING PACING RESPONSE TRANSITIONS", filed Dec. 13, 2019 and providing priority to U.S. Patent application 2021/0016096, published Jan. 21, 2021, the complete subject matter of which are incorporated herein by reference in their entireties.

Embodiments herein utilize P-wave duration (PWD), intrinsic atrial-HIS (AH) delay and intrinsic atrial conduction delay (IACD) to estimate a risk of oversensing atrial activity and to automatically adjust a length of a post atrial ventricular period (PAVP), which in some imitations may be referred to as an atrial oversensing avoidance (AOA) window, as well as adjust a maximum sensitivity setting with ventricular safety pacing. PAVP is an initial time window for the purpose of including atrial components and processing the signals such as the peak and its location etc. The terms PAVP may be used to represent a subset of implementations for an AOA window. For example, the term PAVP may be utilized to refer to implementations in which the corresponding period is used as a device refractory period, whereas the term "AOA window" is more generally used to refer to a PAVP as well as implementations in which the corresponding window period is not limited to only device refractory periods, such as when a sense refractory period could have other functions or features that are not used in connection herewith.

Embodiments address the challenges that arise when a HIS sensing channel is utilized to monitor for RV activity. When the HIS electrode is located in the RA, the HIS sensing channel detects RV activity as a low amplitude component of the CA signal because the ventricular activity is occurring in the far field and exhibits a low-frequency content which is filtered by the HIS sense amplifier. Given that the HIS sensing channel is configured to detect low amplitude, low frequency far field RV signals, the potential arises that the IMD may over sense atrial or HIS activity over the HIS sensing channel. The potential also exists to over sense atrial activity when the HIS electrode is located in the RV. Embodiments herein avoid over sensing the atrial activity on the HIS sensing channel.

During the implant planning process, clinicians select the location (chamber and position within the chamber) at which to position one or more leads and the electrodes thereon. Prior to implanting a leadless IMD and/or subcutaneous IMD and transvenous lead(s), cardiac activity data is collected utilizing an external ECG monitoring system, such as a 12 lead ECG monitor. The ECG monitoring system is used to estimate an individual patient's IACD from the P wave and intrinsic atrioventricular delay (PR). If a patient exhibits a normal IACD (e.g., <=100 ms) that is a desired percentage less than the PR (x % PR), it may be determined that the risk of oversensing atrial activity components is low or can be eliminated by locating the HIS lead in the RA during the implant. Alternatively, if a patient exhibits an IACD having a length that is substantially the same or close to the length of the PR (or if the IACD is larger than the PR), it may be determined that is preferable to locate the electrodes of the HIS lead inside the RV. However, for some patients who receive HIS bundle pacing systems, the risk of oversensing atrial activity components cannot merely be eliminated by locating the HIS sensing electrodes in particular locations.

Instead, in accordance with embodiments herein, methods and systems are provided that automatically determine and adjust the PAVP and sensitivity profile utilized by the HIS sensing channel to identify ventricular activity. The methods and systems herein reduce incidents of oversensing atrial activity components by automatically adjusting the parameters defining the PAVP window and the sensitivity profile (e.g., the sensitivity threshold). Instead of only imposing a blanking window that aligns with the AP spike, embodiments herein start an AOA window (which may also be a PAVP window) upon detection of an intrinsic or paced atrial event (AS or AP). The length of the PAVP window may be varied depending upon whether the atrial event was intrinsic or paced. For example, the duration of the PAVP window may be longer when following a paced atrial event, as compared to the window length when following an intrinsic atrial event. As one nonlimiting example, it may be desirable to utilize a longer PAVP window in connection with a paced atrial event given that the pacing spike and evoked atrial response may potentially give rise to atrial activity components. During the PAVP window, the methods and systems monitor incoming CA signals (over the HIS sensing channel) for amplitude spikes that exceed the current sensitivity threshold. When the CA signal exhibits an amplitude spike that exceeds the sensitivity threshold during the PAVP window, the methods and systems recognize the activity as an atrial activity component, also referred to as atrial cross talk. In response thereto, the sensitivity is lowered, such as by increasing the sensitivity threshold. The atrial activity components/cross talk may persist, such as over the duration of a PAVP window and/or over multiple PAVP windows for successive cardiac beats. Each time an AA component/cross talk is identified, the sensitivity is lowered by increasing the sensitivity threshold (e.g., in a stepwise manner).

Optionally, embodiments herein may define multiple AOA windows that are arranged temporally consecutive with one another. Each time an AA component/cross talk is detected during one AOA window, a next successive AOA window may be initiated until reaching a maximum duration for the multiple AOA windows. When AA component/cross talk are detected over an extended period of time, the methods and systems may implement a predetermined pacing therapy (e.g., a VPB mode with a fixed AP to VP delay such as set at 120 ms or 120 ms—HVs, where HVs corresponds to a duration from a HIS paced event and a V sensed event). For example, the extended period of time may represent a maximum number of AOA windows and/or over a predetermined number of beats.

Embodiments of the present disclosure may be implemented in either a dual chamber or multi-chamber cardiac stimulation device. For example, the present disclosure may be implemented in a rate-responsive multi-chamber cardiac stimulation device. Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. HIS bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown most effective for patients exhibiting a wide QRS complex and left bundle branch block. HBP has also been shown to be effective at narrowing the QRS complex in patients with left bundle branch block, likely due to the anatomy of the HIS bundle, which includes right and left bundle fibers that are longitudinally dissociated. Therefore, what is thought of as left bundle branch block, can be a result of a proximal blockage within the HIS bundle that eventually branches to the left bundle. As a result, by pacing the HIS bundle distal to the blockage, a normalized QRS complex can be achieved in some patients. Theoretically, this pacing mode may provide even better results than known CRT treatments, as activation propagates rapidly through natural conduction pathways.

FIG. 1 illustrates a stimulation device 10 in electrical communication with a patient's heart 12 by way of one or more of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum. To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a HIS bundle lead 21 having a HIS tip electrode 16, such as a helical active fixation device, and a HIS ring electrode 19 located proximal from the HIS tip electrode 16. In certain implementations, the HIS ring electrode 19 is located approximately 10 mm proximal the HIS tip electrode 16. The HIS bundle lead 21 may be transvenously inserted into the heart 12 so that the HIS tip electrode 16 is positioned in the tissue of the HIS bundle. The HIS bundle lead 21 may be located proximate the HIS bundle in the RA or in the RV. Accordingly, the HIS bundle lead 21 is capable of receiving depolarization signals propagated in the HIS bundle or delivering stimulation to the HIS bundle, creating a depolarization that can be propagated through the lower conductive pathways of the right and left ventricles (i.e., the right and left bundle branches and Purkinje fibers).

Figure 2:
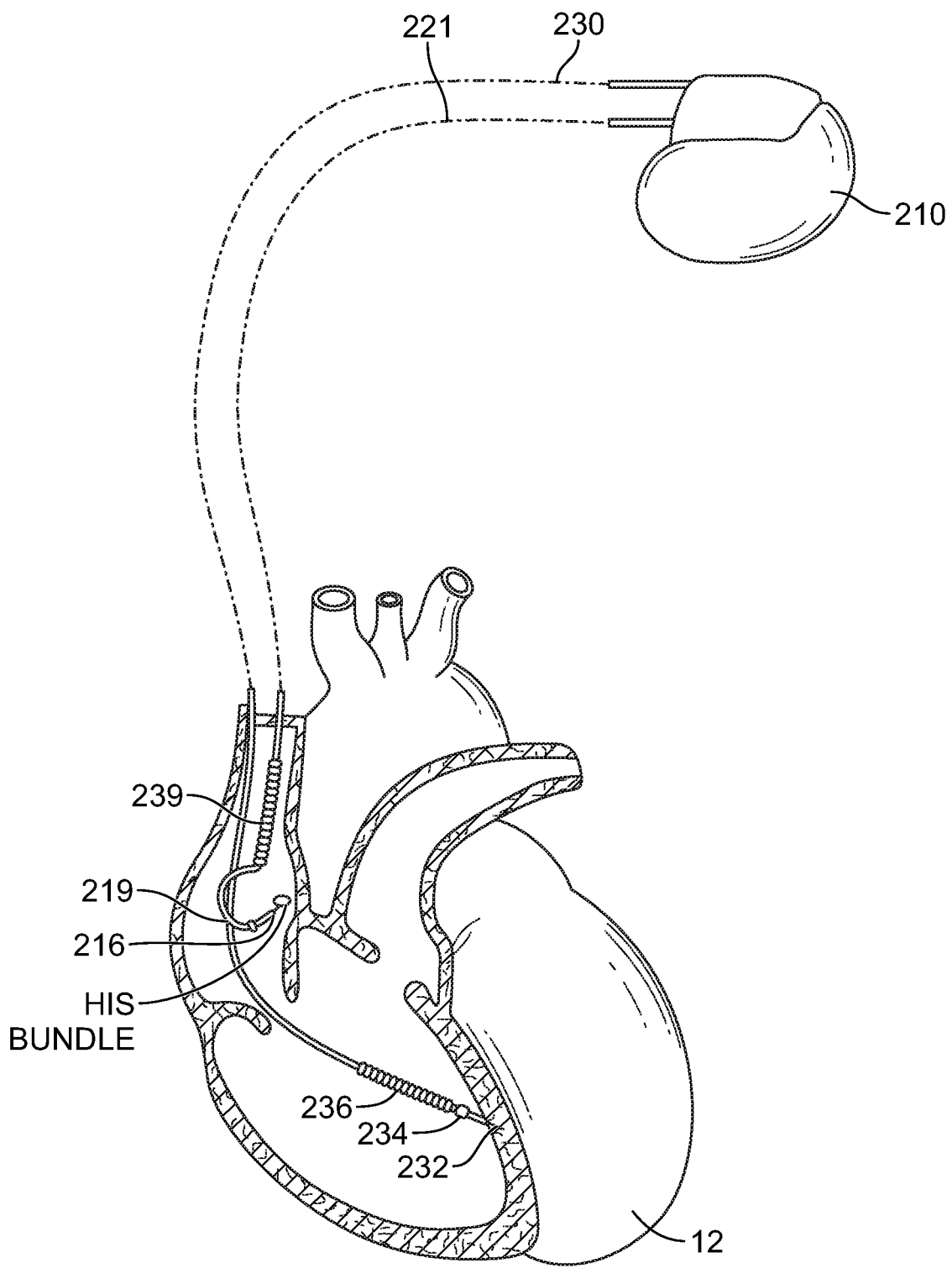
FIG. 2 illustrates a dual chamber stimulation device in communication with one atrium, one ventricle, and the HIS bundle in accordance with embodiments herein.

An alternative embodiment of the present disclosure is shown in FIG. 2 in which a dual chamber stimulation device 210 is in communication with one atrium, one ventricle, and the HIS bundle. Though not explicitly illustrated in FIG. 2, a right atrial lead 20 can be optionally included. In such implementations, the stimulation device 210 maintains communication with the right atrium of the heart 12 via a right atrial lead 20 having at least an atrial tip electrode 22 and an atrial ring electrode 23, and an SVC coil electrode 239. A HIS bundle lead 221, having a HIS tip electrode 216 and a HIS ring electrode 219, is positioned such that the HIS tip electrode 216 is proximate the HIS bundle tissue. The stimulation device 210 is shown in FIG. 2 in electrical communication with the patient's heart 12 by way of a right ventricular lead 230 including a right ventricular tip electrode 232, a right ventricular ring electrode 234, and a right ventricular coil electrode 236.

Optionally, the distal end of the HIS bundle lead 21 is further provided with a non-traumatic conductive surface (also referred to herein interchangeably as a mapping collar). The non-traumatic conductive surface is advantageously used to make electrical measurements that indicate the location of the HIS bundle without having to anchor the HIS bundle tip electrode 16 into the endocardial tissue. The non-traumatic conductive surface and the HIS bundle tip electrode 16 are electrically coupled within the lead body of the HIS bundle lead 21 and together form one conductive element for the purposes of sensing, stimulation, and impedance measurements. Drugs, for example an acute anti-arrhythmic drug such as lidocaine and/or an anti-inflammatory agent such as dexamethasone sodium phosphate, can be stored, for example, within a reservoir (not shown) at the base of the HIS bundle tip electrode 16 for local dispensation.

The HIS bundle lead 21 is also provided with a HIS ring electrode 19. The HIS ring electrode 19 is preferably spaced between approximately 2 mm and 30 mm, but preferably 10 mm, from the HIS tip electrode 16. The HIS ring electrode 19 may function as the return electrode during bipolar sensing, stimulation or impedance measurement operations.

The HIS tip electrode 16 and the HIS ring electrode 19 are each connected to flexible conductors respectively, which may run the entire length of the HIS bundle lead 21. The flexible conductor is connected to the HIS tip electrode 16 and is electrically insulated from the flexible conductor by a layer of insulation. The conductor is connected to the HIS ring electrode 19. The flexible conductors serve to electrically couple the HIS ring electrode 19 and the HIS tip electrode 16 to the HIS ring electrode terminal 51 and the HIS tip electrode terminal 50, respectively. One embodiment of the HIS bundle lead 21 is available from St. Jude Medical CRMD as lead model No. 1488T.

Optionally, the HIS lead may be implanted in the RV with the HIS tip electrode (16 or 216) located proximate the HIS bundle along the septum wall. As a further option, the HIS tip electrode may be configured as and/or provided on, a helical screw at the distal end of the HIS lead, such that the HIS electrode is screwed into the septum wall of the RV proximate the HIS bundle.

Figure 3:
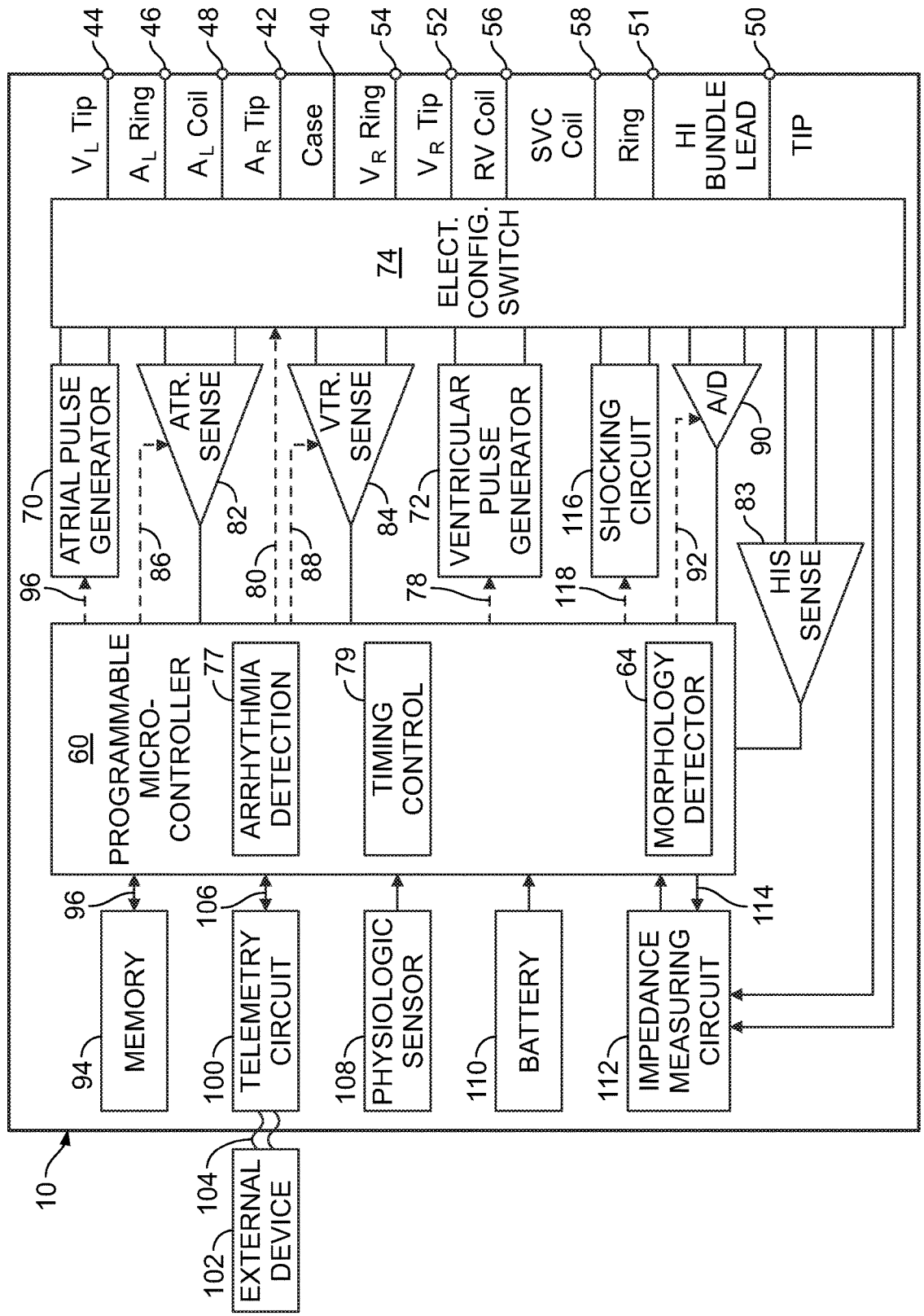
FIG. 3 illustrates a simplified block diagram of the multi-chamber implantable stimulation device of FIG. 1, which is capable of treating both fast and slow arrhythmias with stimulation therapy, including cardioversion, defibrillation, and pacing stimulation in accordance with embodiments herein.

FIG. 3 illustrates a simplified block diagram of the multi-chamber implantable stimulation device 10 of FIG. 1, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chambers) with cardioversion, defibrillation and pacing stimulation. The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 1) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 1).

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively (each shown in FIG. 1). To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 1). To achieve HIS bundle sensing, or sensing and stimulation, the connector further includes a HIS bundle lead tip terminal 50 and a HIS bundle lead ring terminal 51 which are adapted for connection to the HIS tip electrode 16 and the HIS ring electrode 19, respectively (each shown in FIG. 1).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 3, an atrial pulse generator 70 and a ventricular pulse generator 72 generate pacing stimulation pulses for delivery by the right atrial lead 20, the right ventricular lead 30, the coronary sinus lead 24, and/or the HIS bundle lead 21 via an electrode configuration switch 74. It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art. According to one embodiment of the present disclosure, timing control circuitry 79 also controls the onset and duration of a HIS signal sensing window during which a depolarization signal conducted through the AV node to the HIS bundle can be detected. Timing control circuitry 79 also controls a timing delay provided after a detected HIS signal detection, prior to the delivery of a right and/or left ventricular stimulation pulse. The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present disclosure, a HIS sensing circuit 83 is selectively coupled to the HIS bundle lead 21 (shown in FIG. 1) for detecting the presence of a conducted depolarization arising in the atria and conducted to the HIS bundle via the AV node. As used herein, each of the atrial sensing circuit 82, the ventricular sensing circuit 84, and the HIS sensing circuit 83, includes a discriminator, which is a circuit that senses and can indicate or discriminate the origin of a cardiac signal in each of the cardiac chambers. Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart. The atrial and ventricular sensing circuits 82, 84, in turn, receive control signals ever signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90 represented by an ND converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the HIS bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the HIS bundle signal. In one embodiment, an averager is used to determine a sliding average of the HIS bundle signal during a HIS signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The HIS sensing circuit 83 is connected to one or more HIS electrodes, to collectively define the HIS sensing channel that collects at least a portion of the CA signals. The atrial sensing circuit 82 is connected to one or more RA electrodes, to collectively define an RA sensing channel. The memory 94 is configured to store the CA signals obtained over the RA sensing channel and over the HIS sensing channel. The memory also is configured to store program instructions. The microcontroller 60 represents one or more processors that, when executing the program instructions, are configured identify, from at least a portion of the CA signals, at least one of a P-wave duration (PWD), an intrinsic atrial-HIS (AH) delay, or an intrinsic atrial conduction delay (IACD); calculate an atrial oversensing avoidance (AOA) window based on at least one of the PWD, AH delay, or IACD; analyze the CA signals, obtained over the HIS sensing channel during the AOA window, for an atrial activity (AA) AA component. Based on the analyzing operation, the microcontroller 60 is configured to adjust a ventricular event (VE) sensitivity profile utilized by the HIS sensing channel. The microcontroller 60 is further configured to monitor the CA signals, obtained over the HIS sensing channel during an alert window based on the VE sensitivity profile, for a ventricular component indicative of a ventricular event; and manage HIS bundle pacing based on the ventricular event. It is recognized that the one or more processors of the microcontroller 60 may provide instructions to one or more hardware circuits in connection with the operations described herein.

Optionally, the one or more processors of the microcontroller 60 are further configured to set the AOA window to equal at least one of: the PWD when a difference between the AH delay and the PWD is greater than or equal to an alert minimum threshold; or a percentage of the PWD. Optionally, the calculating operation, by the one or more processors, further comprises to set first and second AOA windows that extend continuous with one another following an atrial event, the first AOA window having a length corresponding to at least one of a predetermine time interval or a percentage of the PWD, the second AOA window having a length corresponding to at least one of a percentage of the PWD or the AICD. Optionally one or two AOA window(s) may be utilized. Optionally, the adjusting operation lowers a sensitivity level of the VE sensitivity profile for the HIS sensing channel. Optionally, adjustments to a sensitivity level of the VE sensitivity profile may be made dependent on the peak value of atrial component and/or cross talk. Optionally, the one or more processors are further configured to maintain a count of a number of AA components over a series of beats and, based on the count, determining whether to maintain or change current settings for the length of the AOA window and/or sensitivity profile. Optionally, the AOA window represents the initiation window called a post atrial ventricular period (PAVP) window. Optionally, the one or more processors are configured to perform the analyzing operation over a number of cardiac beats, from which one or more characteristics of interest from the AA components are mathematically combine and utilized to adjust the VE sensitivity profile. Optionally, the one or more processors are further configured to define a post atrial ventricular refractory period (PAVP) window, identify peaks in the CA signal and if that exceed a PAVP sensitivity threshold utilized during the PAVP window, and optionally set AOA window length to PAVP or refine a length of the AOA window based on a timing of a last intercept of the CA signals and a pre-determined thresholds lower than the sensitivity for sensing ventricular signals in alert period. Optionally AOA window can be in between the peak location and PAVP, e.g. AOA=peak location+x % (PAVP−peak location).

Additionally or alternatively, when atria is paced with AP from RA channel for example, a short blanking period is set for the HIS channel (e.g. 15 ms to 30 ms), after which the PAVP window starts.

In the present example, the above operations are performed by an implantable medical device having a housing that includes the memory and the one or more processors, the housing configured to be coupled to the RA electrode and HRIS electrode. Optionally, the IMD may have at least a portion of the one or more processors, while an external device has at least a portion of the one or more processors. The IMD and external device both perform at least a portion of the identifying, calculating, analyzing, adjusting, monitoring and managing operations.

Advantageously, the operating parameters of the implantable device 10 may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 3. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 3 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The device 10 includes two separate connection terminals, one for each of the two flexible conductors that are further connected to switch 74. The two flexible conductors can then be selectively connected as desired to the HIS sensing circuit 83, ventricular pulse generator 72, or impedance measuring circuit 112 for sensing, stimulating, and measuring tissue impedance at the site of the HIS bundle. Using the lead 21, it is possible to effect stimulation with the HIS tip electrode 16 and the HIS ring electrode 19, and to effect sensing with the conductive surfaces. According to another design, the sensing is affected by the conductive surfaces and stimulation is affected by means of the leads other than the HIS lead, for example the right atrial lead 20. For more details regarding a heart electrode equipped with multiple conductive surfaces, reference is made to U.S. Pat. Nos. 5,306,292 and 5,645,580, which are incorporated herein by reference. The HIS tip electrode 16 may be secured in the HIS bundle thereby anchoring the HIS tip electrode 16 in contact with the HIS bundle tissue. The electrogram signal arising from the HIS bundle can then be received by the HIS sensing circuit 83. A bypass filter (not shown) that allows signals ranging from 30-200 Hz to be received may be used to block the high frequency alternating current excitation signals.

Methods to Avoid Over Sensing Atrial Activity Components

Various embodiments are described hereafter for avoiding oversensing of atrial activity components. It should be recognized that the various embodiments may be implemented dynamically within an external or implantable medical device. Embodiments may be implemented continuously and/or based on predetermined criteria in an automatic manner by an IMD. Additionally or alternatively, an external programmer may instruct an IMD to initiate the measurements and calculations described herein. Additionally or alternatively, various embodiments may be implemented entirely, or in part, by an IMD, a local external device, a programmer and/or remote server. For example, an IMD may receive an instruction from a local external device, a programmer and/or remote server to initiate collecting CA signals and/or other information calculated from the CA signals as described herein. The CA signals and/or subsequent calculations may be streamed to a local external device, server and/or programmer. The data streamed from the IMD may be presented on a user interface to allow a clinician to guide HBP parameter settings, including but not limited to the component sensitivity profile, VE sensitivity profile, AOA window length, PAVP window length and the like. Additionally or alternatively, the data streamed from the IMD may be processed on a local external device, programmer and/or remote server to automatically set HBP parameter settings, including but not limited to the component sensitivity profile, VE sensitivity profile, AOA window length, PAVP window length and the like.

In the following discussion of the methods for managing sensing, at least some operations are described with respect to CA signals generally. It is understood that the corresponding operations may be performed on a beat by beat basis and/or may be performed utilizing an ensemble of a predetermined number of beats. Additionally or alternatively, the operations described herein may be performed over multiple beats during one respiration cycle (e.g., 8-10 beats) or more than one respiration cycles. By utilizing an ensemble of beats over a respiration cycle, embodiments account for variations between beats at different phases in the respiration cycle.

Figure 4A:
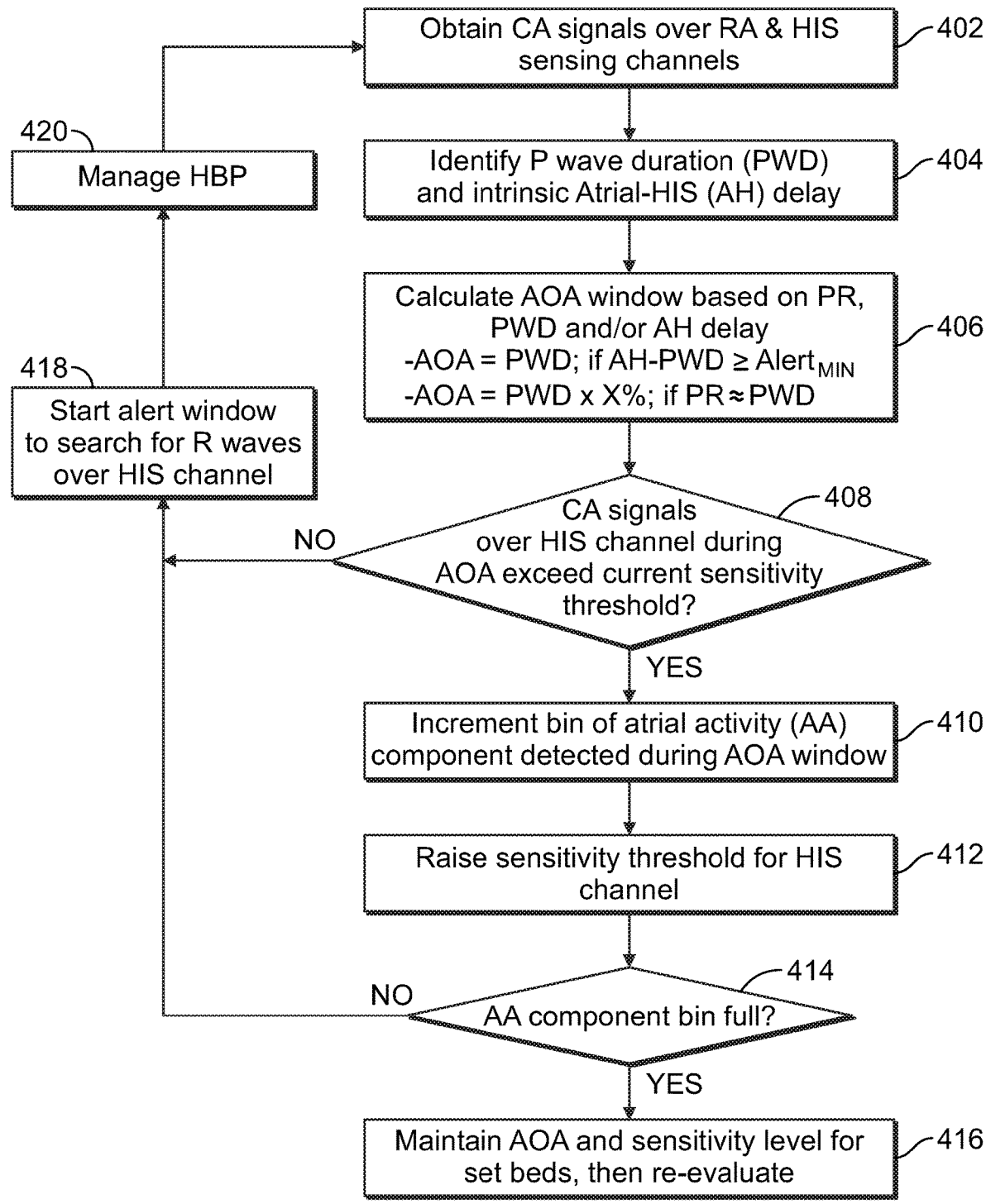
FIG. 4A illustrates a method for managing a sensing operation in connection with HIS bundle pacing in accordance with embodiments herein.

FIG. 4A illustrates a method for managing a sensing operation in connection with HIS bundle pacing in accordance with embodiments herein. The operations of FIG. 4a may be implemented entirely or in part by one or more processors and/or circuitry of an implantable medical device. Optionally, certain operations of FIG. 4A may be implemented by one or more processors of a local external device, clinician programmer and/or remote server and then uploaded to an implantable medical device which in turn implements the remaining operations of FIG. 4. For example, the obtaining, identifying and calculating operations may be performed by a local external device, clinician programmer and/or remote server prior to, during or after implant of an IMD, while the IMD then performs the remaining operations. It is recognized that additional and alternative combinations of the operations may be distributed between one or more external devices and the IMD.

At 402, one or more processors obtain CA signals over an RA sensing channel and over a HIS sensing channel. The RA sensing channel utilizes, and is defined by, one or more RA electrodes located in or proximate to the right atrium. The HIS sensing channel utilizes, and is defined by, one or more HIS electrodes located proximate to the HIS bundle (from a locate in the RA or in the RV).

At 404, the one or more processors determine certain characteristics of interest from the CA signals. For example, the processors may determine a P-wave duration (PWD), intrinsic atrial to HIS (AH) delay and/or intrinsic atrial conduction delay (IACD).

At 406, the one or more processors define an AOA window based on one or more of the PWD, AH delay and/or IACD. By way of example, when a difference between the AH delay and PWD is greater than a predetermined minimum, the length of the AOA window may be set to equal a length of the PWD. Optionally, the length of the AOA window may be defined based on a relation to the PWD. For example, the AOA window may be set to a length corresponding to a percentage X of (or a fix duration less than) the PWD, such as when the interval between a) the peak of an intrinsic atrial event and b) the peak of an intrinsic ventricular event, approximately equals the duration of the PWD. As a nonlimiting example, when utilizing unipolar and bipolar sensing, the P-wave durations may be 114 ms±19 ms (unipolar) vs. 110 ms±20 ms (bipolar). When utilizing bipolar sensing, fewer CA signals (that are remote from the electrodes) are detected over the HIS sensing channel which causes the pulse width duration to be smaller than that of CA signals detected over HIS sensing channel in connection with unipolar sensing.

Optionally, the AOA window may correspond to a PAVP interval, where the IMD utilizes information collected during the PAVP interval for other operations as well. At 404, the processor may set the PAVP window to equal the PWD if AH-PWD>=Alert_min (e.g., 30 ms). Alternatively, the processor may set the PAVP window=PWD*x % (where x %=50-70%) if PR is approximately equal in length to PWD. In the foregoing examples, the PWD is measured. Optionally, as an alternative, the PWD may be set to various default lengths based on whether an intrinsic atrial event is sensed (AS) or a paced atrial event (AP) is delivered. For example, the default PWD may be set to 60 ms for AS and 90 ms for AP.

Optionally, at 404 the one or more processors may also set one or more parameters of one or more sensitivity profiles to a default threshold. For example, the operations herein may utilize one sensitivity profile during the AOA window and a different sensitivity profile during a subsequent alert window while searching for a ventricular event (VE). Accordingly, a first or component sensitivity threshold may be utilized during the AOA window when searching for AA components, while a second or VE sensitivity threshold is utilized during the alert window while searching for ventricular activity. For example, the sensitivity profile for the AOA window and/or the alert window may represent "straight-line" profiles that have sensitivity thresholds set to default levels (e.g., 0.5 mV, 1.0 mV, etc.). As a further option, the sensitivity threshold may vary over a range between (e.g., 0.3 mV and 3 mV). Optionally, the sensitivity threshold initially set for the AOA window may be the same as used during the alert window. Optionally, the dynamic range utilized in connection with the AOA window (while searching for AA components) may be fixed at the same values associated with default or programmed values.

At 408, the process determines whether CA signals, that are sensed over the HIS sensing channel during the AOA window, exceed the current sensitivity threshold. At 408, the HIS sensing circuit and/or processors analyze the CA signals, obtained over the HIS sensing channel during the AOA window, for AA components. An AA component may be represented by one or more spikes in the CA signal that exceed the corresponding sensitivity threshold. For example, the HIS sensing circuit and/or processors may determine whether positive or negative peaks in the CA signals exceed 0.5 mV. When the AOA window expires without detecting one or more AA components, flow moves to 418. The determination at 408 may be based on a single AA component or multiple AA components during a current beat, such as when a desired number of peaks (e.g., one or more) in the CA signals exceed the component sensitivity threshold. Optionally the PAVP or AOA window is initiated by atrial a sensed or paced event in RA channel, without a need for the CA signals crossing the current sensitivity threshold. The HIS sensing circuit and/or processors analyze the CA signals, obtained over the HIS sensing channel during the AOA window, and compare the peak(s) of the CA signals to the sensitivity threshold.

At 418, the one or more processors initiate an alert window, during which the process monitors CA signals over the HIS sensing channel for ventricular components indicative of ventricular events (e.g., a peak in the R-wave). The alert window represents an interval in which the process searches for ventricular activity. When the HIS sensing channel is located proximate the HIS bundle, ventricular components sensed over the HIS sensing channel are detected as far field signals. While listening for ventricular components over the HIS sensing channel, the HIS sensing circuit uses a sensitivity profile having a predetermined VE sensitivity threshold. The predetermined VE sensitivity threshold may be the same as or different from the component sensitivity threshold utilized to search for atrial activity components at 408.

At 420, the one or more processors of the IMD manage HIS bundle pacing based on the CA signals sensed over the HIS sensing channel during the alert window.

Returning to 408, when the processors identify an AA component during the AOA window, flow moves to 410. At 410, the one or more processors update a count of a number of AA components that have been detected, during AOA windows, over a select period of time or beats. For example, the processors may increment a bin that tracks the number of AA components each time operation reaches 410.

At 412, the one or more processors change one or more sensing parameters of the HIS sensing circuit that define the VE sensitivity profile. For example, the processors may change the VE sensitivity threshold for the VE sensitivity profile to be used during a subsequent alert window. At 412, the processors "increase" or "raise" the VE sensitivity threshold, thereby "lowering" the sensitivity of the HIS sensing channel. For example, the processors may directly change the VE sensitivity threshold to a predetermined value (e.g., maxSen=1 mV~3 mV). Alternatively, the processors may lower the VE sensitivity threshold based on an amplitude of a peak detected in the CA signals during the AOA window. For example, when a peak during the AOA window is 0.65 mV, the processors may set the VE sensitivity threshold to be greater by a predetermined amplitude (e.g., 0.65 mV+0.2 mV=0.85 mV).

At 414, the one or more processors determine whether the AA component bin is full or has exceeded a predetermined count (e.g., AA components were counted during 3-5 beats). When the AA component bin is not full, flow moves to 418. At 418, the one or more processors start an alert window (also referred to as a VE search window). During the alert or VE search window, the one or more processors monitor incoming CA signals obtained over the HIS sensing channel for ventricular components indicative of ventricular events. At 420, the one or more processors manage HIS bundle pacing based on the CA signals collected during the alert window. When flow moves from 414 to 418, the process searches for ventricular components utilizing the VE sensitivity threshold set at 412 which may have a higher sensitivity threshold (e.g., lower sensitivity) than a default VE sensitivity threshold (e.g., when flow moves from 408 to 418).

Returning to 414, when the AA component bin fills and flow moves to 416, the process continues operation for a desired number of beats (e.g., 256 beats) or until other criteria are met (e.g., number of inhibited HIS pacing beats or by additional sensors such as accelerometers for heart rate or activity, posture etc), while maintaining current settings for the duration of the AOA window (set at 406) and the component sensitivity threshold (set at 412). After the desired number of beats, the operations of FIG. 4A may be repeated to reevaluate the AOA window duration and sensitivity to be utilized during the alert window.

Additionally or alternatively, in some instances, a patient's cardiac behavior may give rise to the AOA window being calculated to have a duration that is near or the same length as the IMD pre-programmed AH delay (e.g., the AH delay that is programmed as the delay between a HIS bundle pacing pulse and a ventricular pacing pulse in the absence of an intrinsic VE during the alert window). Also, in some instances, the patient's cardiac behavior may exhibit amplitudes for AA components that are close to or greater than an amplitude of VE components (sensed during the alert window). When both the AOA window is near the length of the programmed AH delay and the AA component amplitude is close to or greater than the amplitude of intrinsic VE components, the HBP operation at 420 may initiate a predetermined pacing mode. For example, the IMD may simply deliver HIS bundle pacing at a HIS site and a V site at a fixed delay regardless of the programmed AH delay.

Figure 4B:
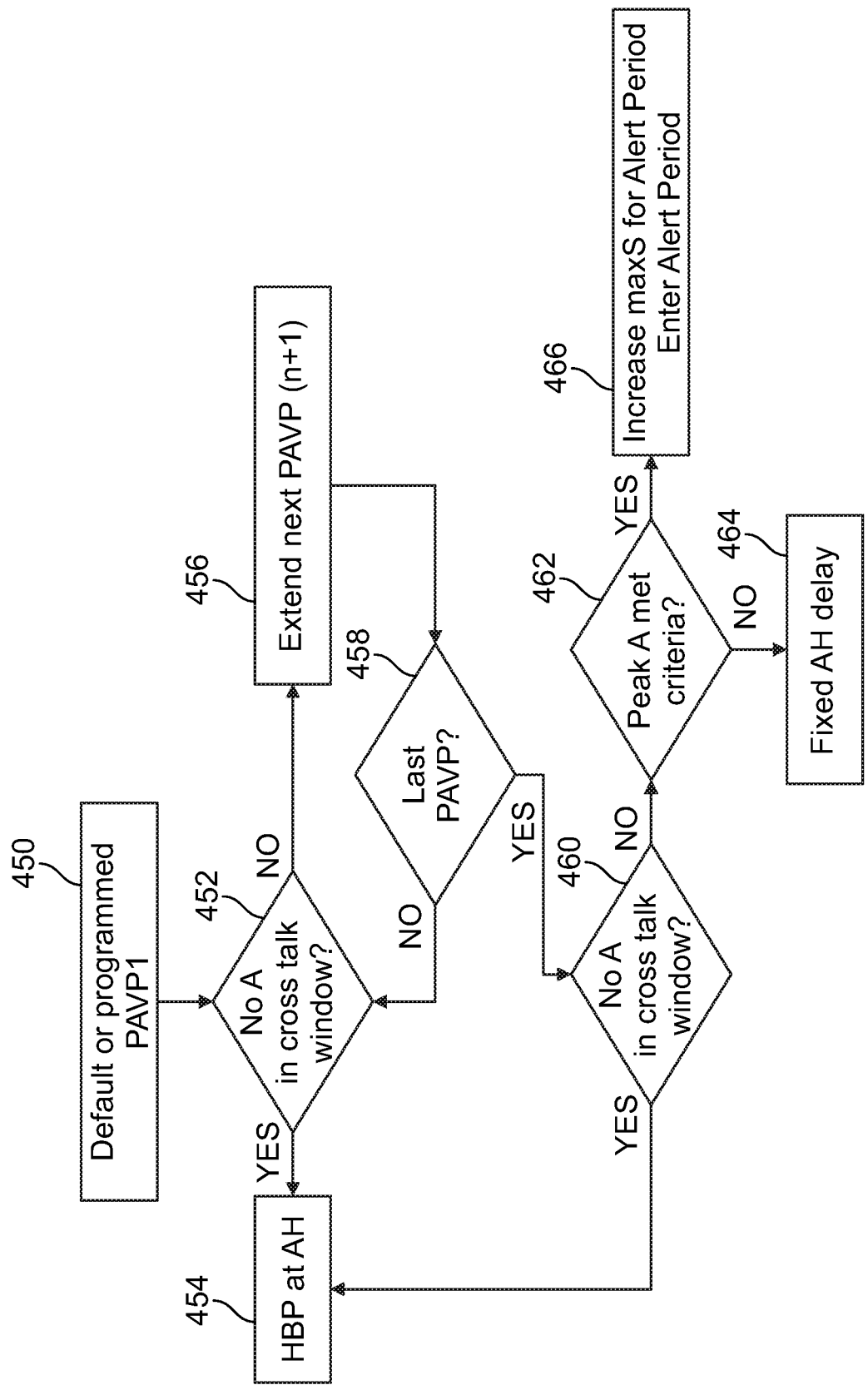
FIG. 4B illustrates a method for managing a sensing operation in connection with HIS bundle pacing in accordance with embodiments herein.

FIG. 4B illustrates a method for managing a sensing operation in connection with HIS bundle pacing in accordance with alternative embodiments herein. At 450, the one or more processors set the PAVP to a default or programmed duration. While the example of FIG. 4B is described in connection with a PA VP, it is understood that the embodiment may be utilized more generally with an AO a window that is not limited to a device refractory period. In the example of FIG. 4B, the PAVP duration equals the length of the AOA window. At 452, the one or more processors analyze incoming CA signals to determine whether an AA component is detected during the PAVP (more generally AOA window). If so, flow moves to 454 and His bundle pacing is delivered at the end of the AH delay. Alternatively, when no AA component is detected during the PAVP, flow moves to 456. At 456, the one or more processors determine whether to extend the analysis to a next consecutive PAVP. As described in connection with embodiments herein, more than one PAVP may be applied consecutively with one another. At 458, the one or more processors determine whether the current PAVP represents the last PAVP (e.g. when a limited number of PAVPs are to be utilized). If the current PAVP is not the last, flow returns to 452 where the one or more processors determine whether an AA component is detected during the current PAVP.

When the current PAVP represents the last, flow continues to 460. At 460, the one or more processors determine whether an AA component is detected during the current PAVP. If so, flow returns to 454 where HBP pacing is delivered. If not, flow continues to 462. At 462, the one or more processors determine whether the peak amplitude of the AA component satisfies the criteria (e.g. exceeds a upper threshold). If the peak amplitude of the AA component does not exceed the criteria, flow moves to 464. If the peak amplitude of the AA component exceed the criteria, flow moves to 466.

At 464, the IMD implements HBP pacing utilizing a fixed AH delay (e.g. in AH delay that is preprogrammed). At 466, the one or more processors increase the maximum sensitivity for the alert period and then enters an alert period duration.

Figure 5:
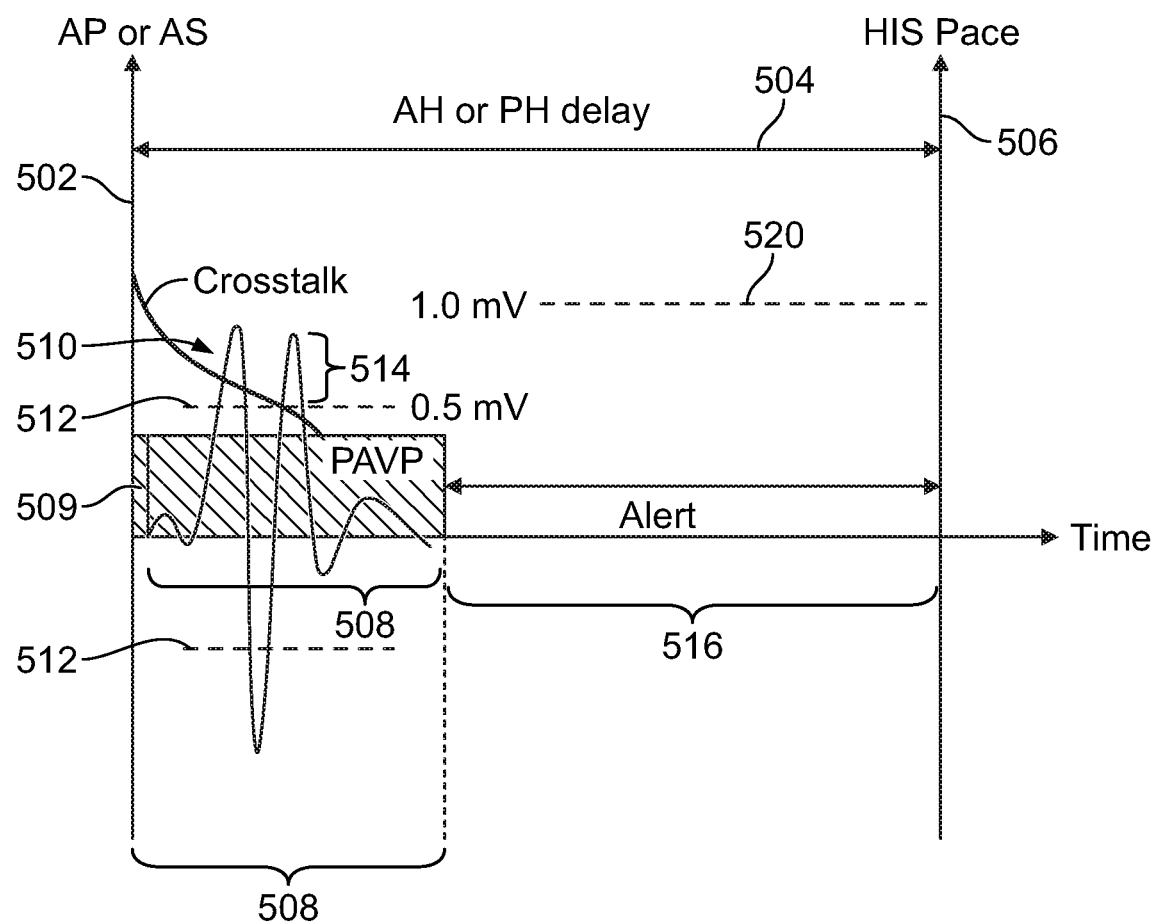
FIG. 5 illustrates a timing diagram for an example implementation of the method of FIG. 4a in accordance with embodiments herein.

FIG. 5 illustrates a timing diagram for an example implementation of the method of FIG. 4A. FIG. 5 illustrates a CA signal collected over one cardiac cycle beginning with an atrial paced or sensed event (AP or AS) at 502. A delay 504 is programmed into the device. The delay 504 may be the same or different depending on whether the atrial event is sensed or paced (e.g., AH=$1^{st}$ delay; PH=$2^{nd}$ delay). If an intrinsic ventricular event is not detected before the end of the AH or PH delay 504, the IMD will deliver a HIS paced event at 506. With reference to the operations of FIG. 4B, when the AP or AS atrial event is detected, an AP blanking interval 509 is initiated, followed by initiation of a PAVP 508 (corresponding to the AOA window determined in connection with FIG. 4A). Optionally, the AP blanking window 509 may only be included following a paced atrial event, while intrinsic sensed atrial events may not include an AP blanking window 509 in front of the PAVP window 508. In the embodiment of FIG. 5, the AOA window is utilized as a PAVP window in connection with other PAVP related operations performed by the IMD. Accordingly, the window 508 may be referred to as an AOA window (more generally) or a PAVP window (as in the more specific embodiment of FIG. 5).

The duration of the window 508 is previously set based on the operations at 402-406 (FIG. 4A). At 408, the one or more processors monitor CA signals 510 that are collected over the HIS sensing channel during the window 508. In the example of FIG. 5, a component sensitivity threshold is set (e.g., 0.5 mV) as noted at sensitivity threshold 512. At 408, the one or more processors determine the peak of the CA signals and that the CA signal 510 includes an AA component 514 (e.g., the CA signal exceeds the component sensitivity threshold 512). Optionally, a blanking period (e.g., 15-30 ms) may be added. Accordingly, flow moves to 410 (FIG. 4A) where the AA component bin is incremented. Optionally, the binning operation at 410 and the "bin full" test at 414 may be omitted entirely. At 412, the sensitivity to be applied during the alert (VE search) window 516 is lowered by increasing the VE sensitivity threshold (e.g., to 1.0 mV). During the alert window 516, CA signals sensed over the HIS sensing channel are compared to the VE sensitivity threshold 520. When the CA signal exceeds the VE sensitivity threshold 520, the processors interpret the CA signal segment (occurring during the alert window) to include a ventricular component indicative of an intrinsic ventricular event and thus no ventricular paced event is delivered. In the example of FIG. 5, the alert window 516 does not include a CA signal segment that exceeds the VE sensitivity threshold 520 and thus a ventricular pacing pulse is delivered at 506 (corresponding to the operation at 420 in FIG. 4).

Figure 6:
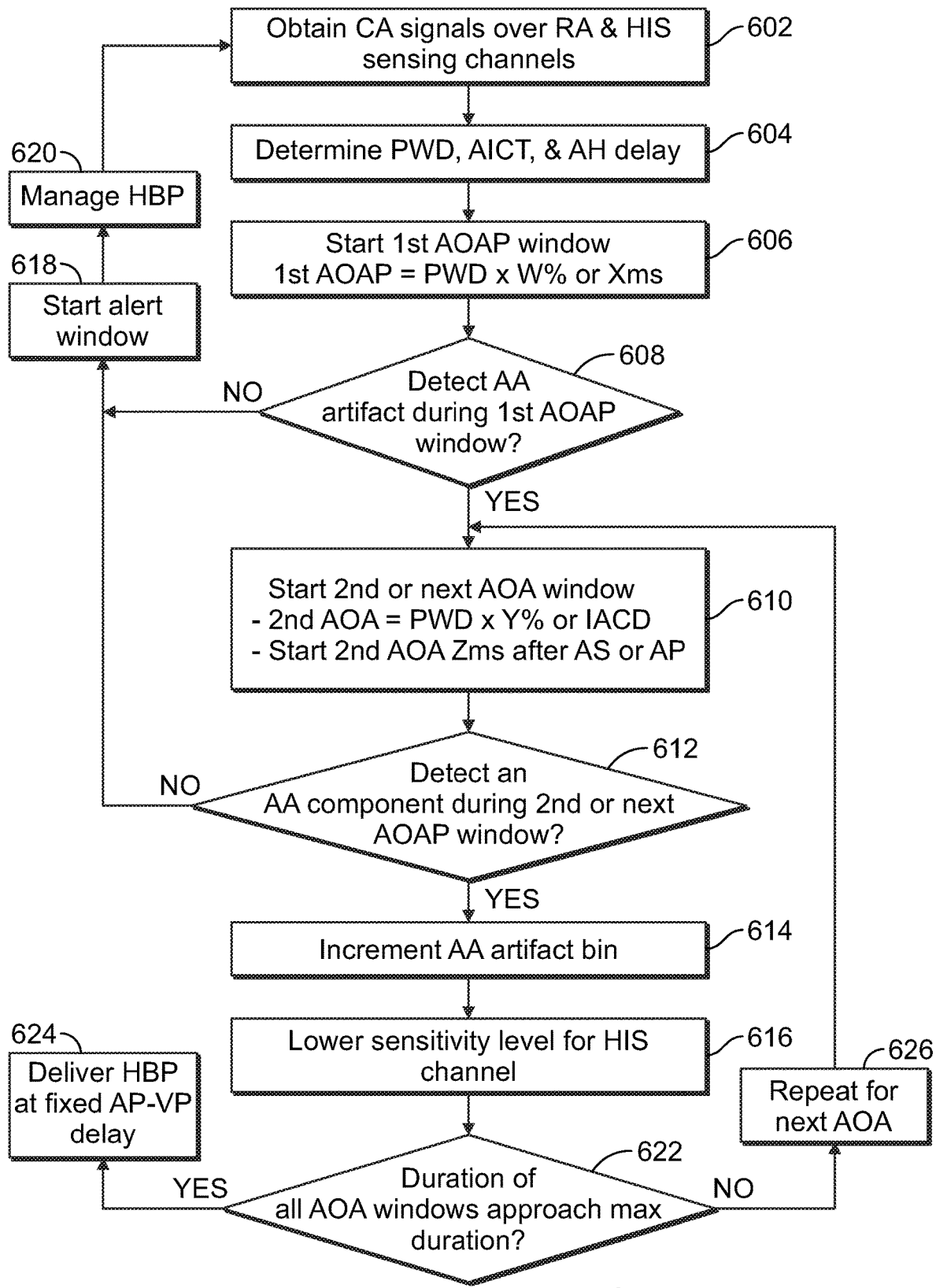
FIG. 6 illustrates a method for managing a sensing operation in connection with HIS bundle pacing in accordance with embodiments herein.

FIG. 6 illustrates a method for managing a sensing operation in connection with HIS bundle pacing in accordance with embodiments herein. The operations of FIG. 6 may be implemented entirely or in part by one or more processors and/or circuitry of an implantable medical device. Optionally, certain operations of FIG. 6 may be implemented by one or more processors of a local external device, clinician programmer and/or remote server and then uploaded to an implantable medical device which in turn implements the remaining operations of FIG. 6. For example, the obtaining, identifying and calculating operations may be performed by a local external device, clinician programmer and/or remote server prior to, during or after implant of an IMD, while the IMD then performs the remaining operations. It is recognized that additional and alternative combinations of the operations may be distributed between one or more an external device and the IMD.

At 602, one or more processors obtain CA signals over an RA sensing channel and over a HIS sensing channel. At 604, the one or more processors determine certain characteristics of interest from the CA signals (e.g., PWD, intrinsic AH delay and IACD). At 606, the one or more processors define a first AOA window based on one or more of the PWD, intrinsic AH delay and/or intrinsic IACD. By way of example, the length of the first AOA window may be set to equal a percentage of the PWD or a difference between the PWD and a fixed offset (such as the case of AP and a blanking period preceding the AOA window). Optionally, when an atrial paced event is delivered, the AOA window may be preceded by a short blanking window (e.g., 15-30 ms). Optionally, as an alternative, the PWD may be set to various default lengths based on whether an intrinsic atrial event is sensed (AS) or a paced atrial event (AP) is delivered.

Optionally, at 604 the processor may also set one or more parameters of the component and VE sensitivity profiles to default thresholds. A first component sensitivity threshold may be utilized during the first AOA window (e.g., 0.5 mV, 1.0 mV, etc.). Optionally, the sensitivity threshold initially set for the first AOA window may be the same as (or different from) the sensitivity threshold used during the second, third, etc. AOA windows.

At 608, the one or more processors determine whether CA signals, that are sensed over the HIS sensing channel during the first AOA window, exceed the current sensitivity threshold. At 608, the processors analyze the CA signals, obtained over the HIS sensing channel during the first AOA window, for AA components. When the first AOA window expires without detecting one or more AA components, flow moves to 618. The determination at 608 may be based on a single AA component or multiple AA components, such as when a desired number of peaks (e.g., one or more) in the CA signals exceed the component sensitivity threshold.

At 618, the one or more processors initiate an alert window, during which the IMD monitors CA signals over the HIS sensing channel for ventricular components indicative of ventricular events (e.g., above ventricular sensitivity in the R-wave). The alert window represents an interval in which the processors search for ventricular activity. The predetermined VE sensitivity threshold may be the same as or different from the first component sensitivity threshold. At 620, the one or more processors of the IMD manage HIS bundle pacing based on the CA signals sensed over the HIS sensing channel during the alert window.

Returning to 608, when the processors identify an AA component during the first AOA window, flow moves to 610. At 610, the one or more processors define a second AOA window based on one or more of the PWD, intrinsic AH delay and/or IACD. By way of example, the length of the second AOA window may be set to equal a percentage of the PWD (that differs from the percentage used at 606) or a difference/sum between the PWD and a fixed offset (e.g. the case of AP and a blanking period preceding AOA). Optionally, as an alternative, the second AOA window may be set to start a fixed time (in milliseconds) after the AS or AP event.

At 612, the one or more processors determine whether CA signals, that are sensed over the HIS sensing channel during the second AOA window, exceed the second component sensitivity threshold. At 612, the processors analyze the CA signals, obtained over the HIS sensing channel during the second AOA window, for AA components. When the second AOA window expires without detecting one or more AA components, flow moves to 618. When one or more AA components are detected during the second AOA window, flow moves to 614.

At 614, the one or more processors update a count of AA components that have been detected, during the first and second AOA windows, over a select period of time or beats. For example, the processors may increment a bin that tracks the number of AA components during the first, second, etc. AOA windows each time the operation reaches 614. Optionally, when more than two AOA windows are utilized, the count of AA components may track the multiple AOA windows.

At 616, the one or more processors change one or more parameters that define the VE sensitivity profile. For example, the processors "increase" or "raise" the VE sensitivity threshold, thereby "lowering" the sensitivity of the HIS channel to components within the CA signals.

At 622, the one or more processors determine whether the duration of the AOA windows is approaching, has reached or exceeds a maximum duration for the group of AOA windows. When the duration of the group of AOA windows reaches the maximum duration, flow moves to 624. At 624, the IMD delivers HIS bundle pacing at a fixed delay between atrial paced events and ventricular paced events. Optionally, the operation at 624 may be omitted and flow may move directly from 622 back to 618.

Returning to 622, when the duration of the AOA windows has not yet reached the maximum duration, flow moves to 626. At 626, the above operations are repeated for a next AOA window. For example, the duration of the next AOA window is defined, such as based on the PWD, IACD and/or intrinsic AH delay.

Optionally, when a third or later AOA window is utilized, the sensitivity threshold assigned for the VE sensitivity threshold may be also applied during the third or later AOA window. If no AA activity is sensed in the third AOA window (e.g., the CA signal exceeds the VE sensitivity threshold), flow may move to 618 to start the alert window. If the AA is still sensed, the max peak in the window is measured and used to set up the new sensitivity value as max AA peak+margin (e.g. 0.1-0.3 mV). Alternatively, when activity is sensed in the third AOA window (e.g., the CA signal does not exceed the VE sensitivity threshold), or max AA peak is similar to or greater than V peak, flow may move to 624 where HBP pacing is applied at a fixed AP-VP delay.

In accordance with some embodiments, a small delay may occur between a time at which an atrial paced event is delivered from the RA lead until AA components may begin to appear on the HIS sensing channel.

Figure 7A:
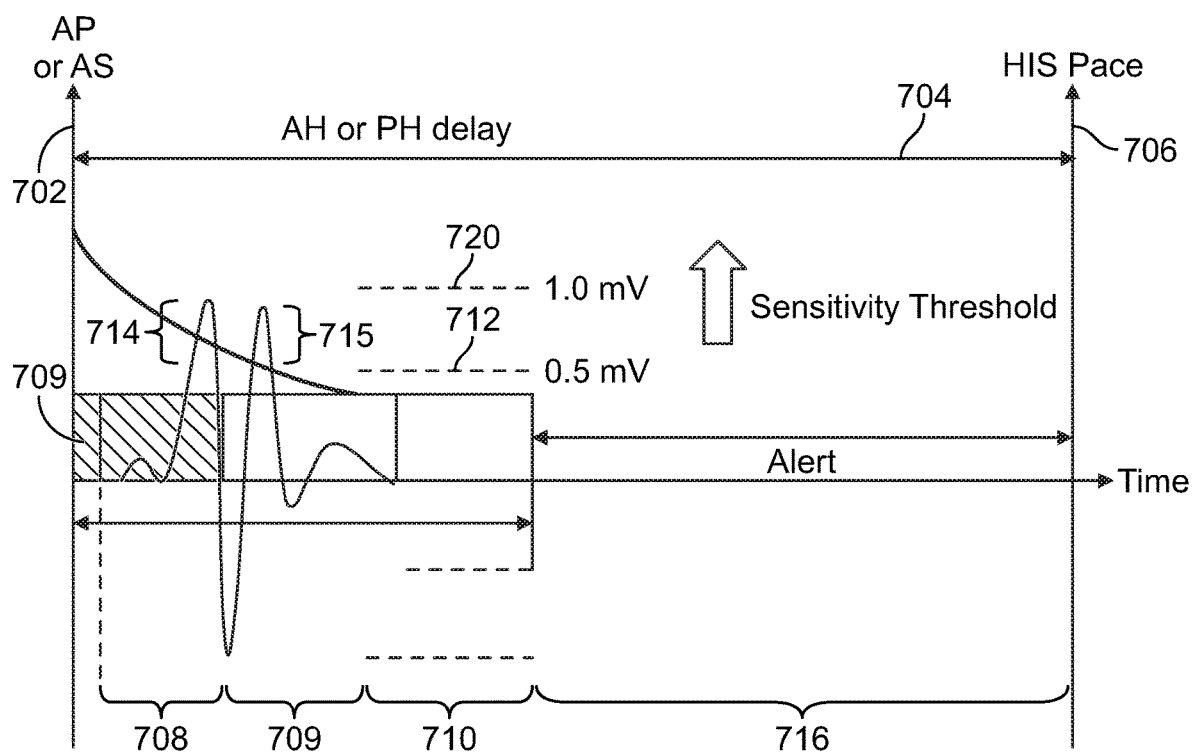
FIG. 7A illustrates a timing diagram for an example implementation of the method of FIG. 6 in accordance with embodiments herein.

FIG. 7A illustrates a timing diagram for an example implementation of the method of FIG. 6. FIG. 7A illustrates a CA signal collected over one cardiac cycle beginning with an atrial paced or sensed event (AP or AS) at 702. A delay 704 is programmed into the device and it can be set long enough (>intrinsic AH or >AVs) for this measurement. The delay 704 may be the same or different depending on whether the atrial event is sensed or paced (e.g., AH=$1^{st}$ delay; PH=$2^{nd}$ delay). If an intrinsic ventricular event is not detected before the end of the AH or PH delay 704, the IMD will deliver a ventricular paced event at 706. With reference to the operations of FIG. 6, when the AP or AS atrial event is detected, an AP blanking window 709 is initiated, followed by a first AOA window 708. Optionally, the AP blanking window 709 may only be included following a paced atrial event, while intrinsic sensed atrial events may not include an AP blanking window 709 in front of the AOA window 708. The duration of the AOA window 708 is previously set based on the operations at 602-606 (FIG. 6). At 608, the one or more processors monitor CA signals 710 that are collected over the HIS sensing channel during the first AOA window 708. In the example of FIG. 7, a first component sensitivity threshold is set (e.g., to correspond to 0.5 mV) as noted at first sensitivity threshold 712. At 608, the one or more processors determine the maximum peak 714 of the CA signal 710 (rectified or absolute values) and that the CA signal 710 includes an AA component 714 (e.g., the CA signal exceeds the component sensitivity threshold 712). There are multiple approaches in determining the max AA peak and cross the sensitivity value. One is to measure the max peak in the assigned window and then compare to the sensitivity value. Accordingly, flow moves to 610 (FIG. 6) and the second AOA window is defined.

At 612, the one or more processors monitor the CA signals 710 over the second AOA window 709. A second AA component 715 is detected during the second AOA windows 709. Accordingly, in the operations of FIG. 6, flow moves to 614 where the AOA components are counted and the VE sensitivity is lowered by raising the VE sensitivity threshold. At 616, the sensitivity to be applied during the alert (VE search) window 716 is lowered by increasing the VE sensitivity threshold 720 (e.g., to 1.0 mV). During the alert window 716, CA signals sensed over the HIS sensing channel are compared to the VE sensitivity threshold 720. When the CA signal exceeds the VE sensitivity threshold 720, the processors interpret the CA signal segment (occurring during the alert window) to include a ventricular component indicative of an intrinsic ventricular event and thus no ventricular paced event is delivered. In the example of FIG. 7, the alert window 716 does not include a CA signal segment that exceeds the VE sensitivity threshold 720 and thus a ventricular pacing pulse is delivered at 706 (corresponding to the operation at 620 in FIG. 6).

Figure 7B:
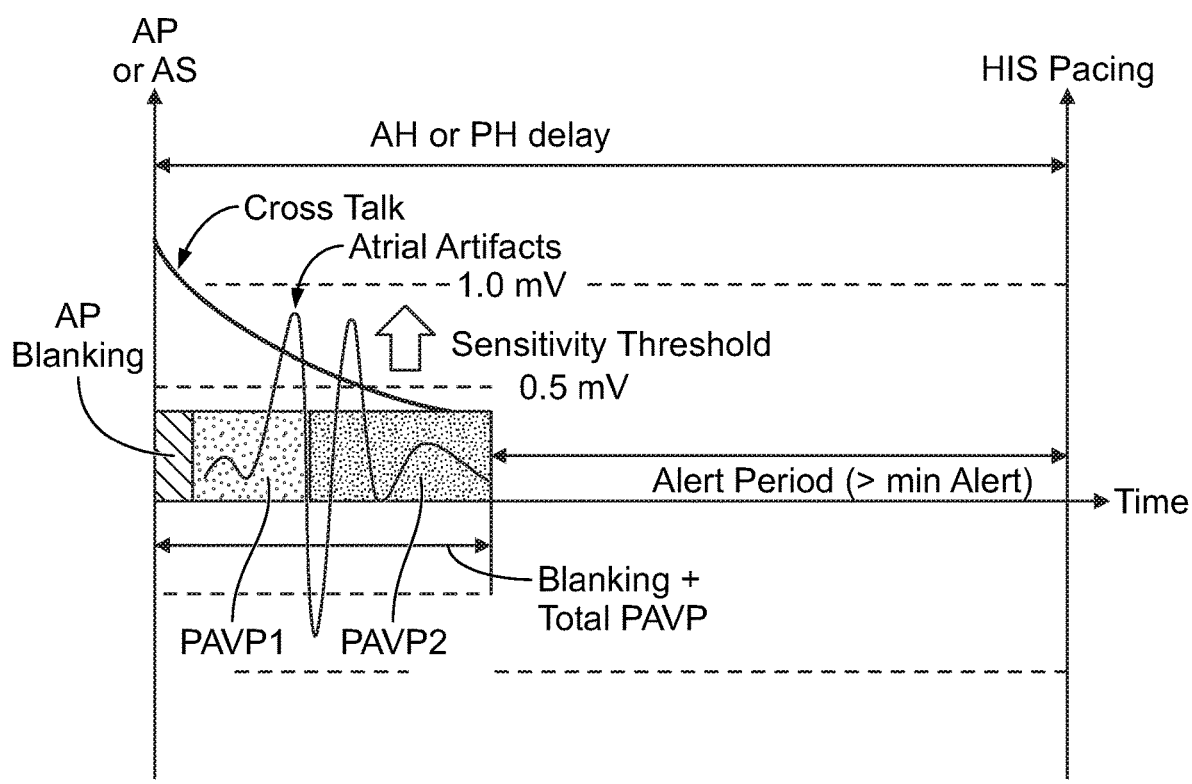
FIG. 7B illustrates a timing diagram for an example implementation in accordance with embodiments herein.

FIG. 7B illustrates a timing diagram for an example implementation in accordance with embodiments herein. Even though multiple PAVPs are illustrated, two PAVPs may be preferred. As an example, a maximum allowed length of PAVP is based on IACD or PWD and the AH delay is divided into two PAVPs. If an AA component is detected in PAVP1, PAVP2 is used and a max peak (rectified or absolute AA) is measured for setting new sensitivity.

Next, an alternative embodiment as discussed in connection with FIGS. 8-12 that applies atrial over sensing avoidance protection in connection with two sensing channels.

Figure 8:
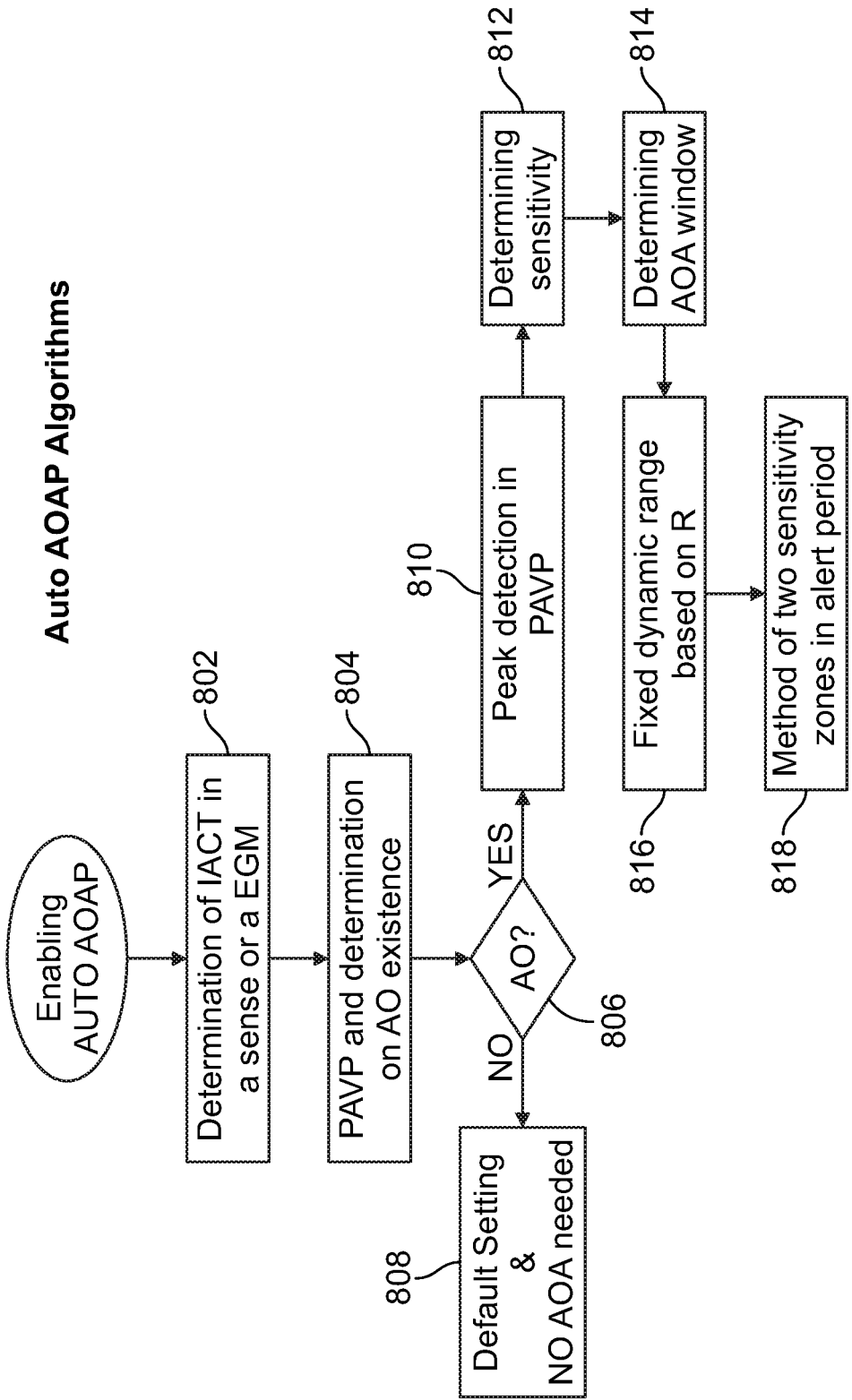
FIG. 8 illustrates a method for managing a sensing operation in connection with HIS bundle pacing in accordance with embodiments herein.
Figure 9:
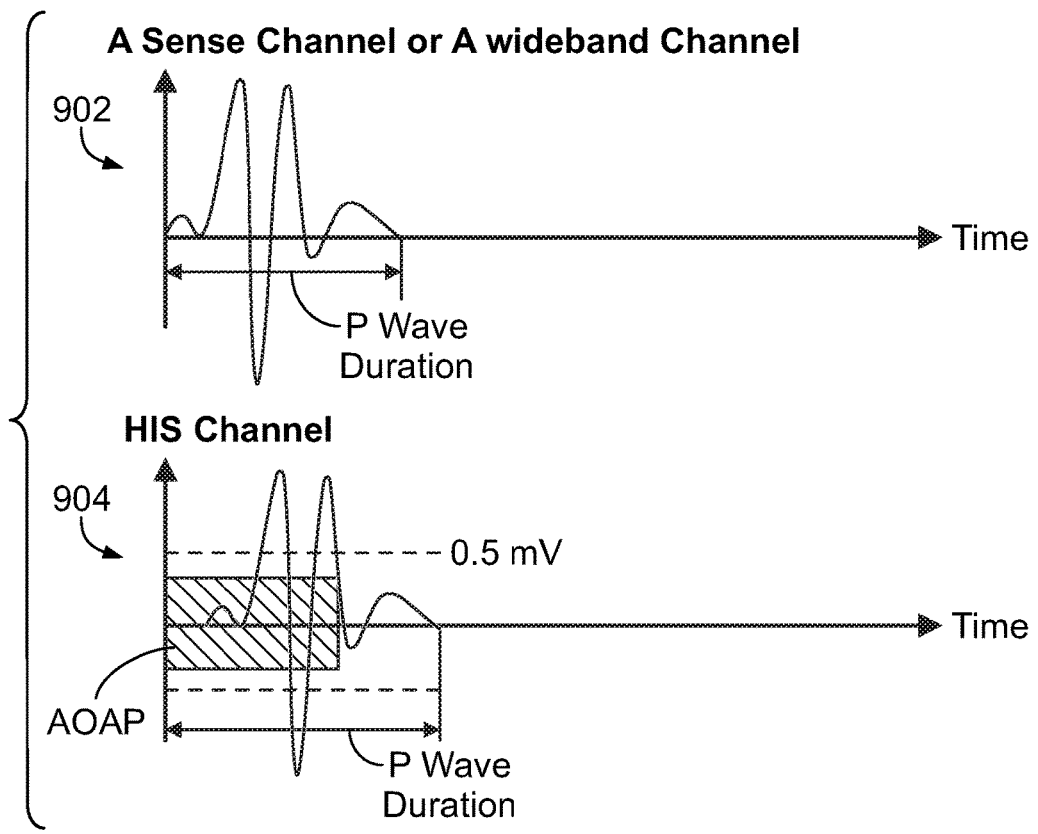
FIG. 9 illustrates examples of CA signals sensed over an atrial sensing channel and a HIS sensing channel in accordance with embodiments herein.

FIG. 8 illustrates a method for managing a sensing operation in connection with HIS bundle pacing in accordance with an alternative embodiment herein. At 802, one or more processors obtain CA signals over an atrial sensing channel. FIG. 9 illustrates examples of CA signals sensed over an atrial sensing channel 902 and a HIS sensing channel 904. At 802, the one or more processors determine an IACD from the CA signals sensed over the atrial sensing channel. At 804, the one or more processors utilize a PAVP window to monitor CA signals sensed over the HIS sensing channel 804. At 806, the process determines whether atrial over sensing is occurring after the atrial sensed or paced event on the atrial sensing channel. At 806, when no atrial oversensing occurs, flow moves to 808. At 808, the one or more processors use default settings and no AOA window is needed. Alternatively, at 806, when atrial oversensing is occurring, flow moves to 810.

The operations at 810-818 set a select group of parameters. At 810, the maximum peaks in the CA signals are detected over a PAVP window. At 812, a sensitivity is determined for the AOA window. At 814, the duration of the AOA window is determined, such as based on an occurrence of a last intercept to a threshold set below current sensitivity for V sense during the PAVP window. Optionally the AOA window can be set as the end between the peak location and PAVP, e.g. AOA window=peak location+x % (PAVP−peak location).

Figure 10:
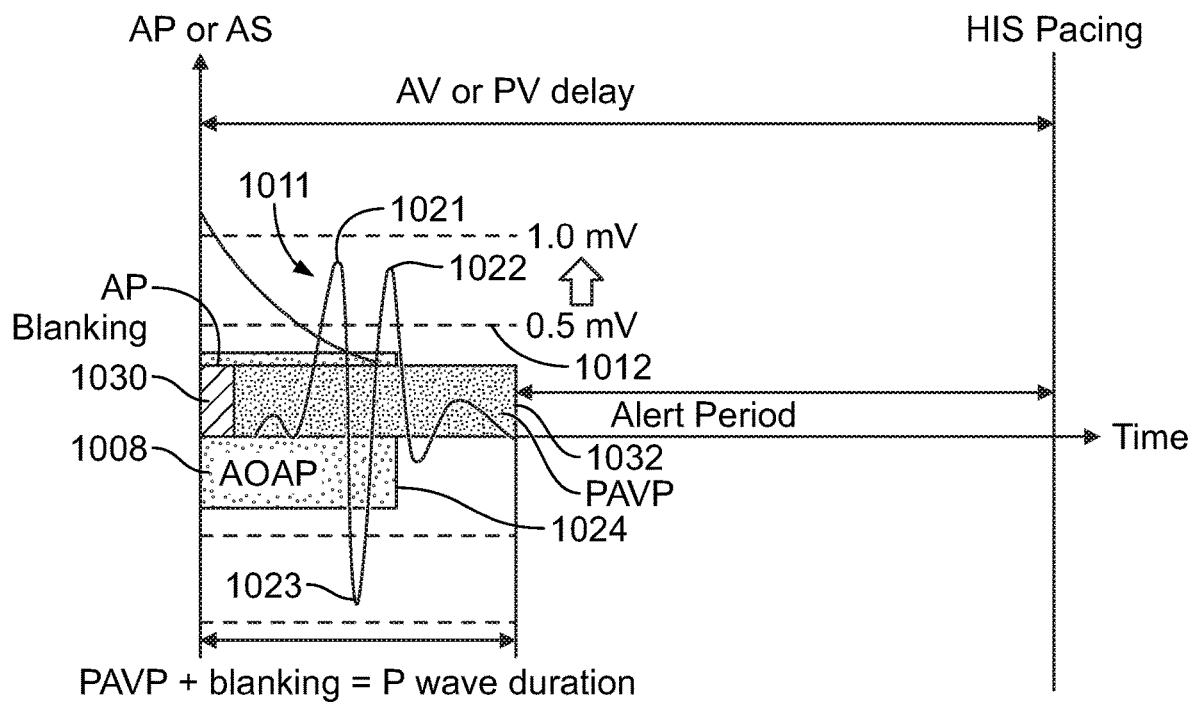
FIG. 10 illustrates a PAVP window is set based on the P-wave duration in accordance with embodiments herein.

With reference to FIG. 10, when detecting atrial oversensing, first a PAVP window is set based on the P-wave duration or IACD. The window can be triggered by an atrial sensed or paced event with a RA lead. During the PAVP window, one or more processors within the IMD can detect intercept crossings (by the CA signals) over a PAVP sensitivity threshold (if present). When the CA signal crosses the sensitivity threshold, the IMD detects the maximum peak of the rectified signal during the PAVP window. Optionally the IMD can detect the maximum peak and its location in a PAVP without firstly detecting crossing the sensitivity threshold. The max peak value can be used for comparisons of the sensitivity threshold and determine if it is over. The maximum peak value is then utilized to reduce a sensitivity threshold used subsequently during the AOA and/or alert windows. Optionally, a duration of the AOA window may be determined based solely on the P-wave duration and/or on alternative or additional parameters. When a short AOA window is desired, the duration of the AOA window may be set based on the last intercept point of the CA signal and the sensitivity threshold minus a delta, or simply the peak location+x % (PAVP−max peak location) for ease of hardware implementation As shown in FIG. 10, the CA signal 1011 crosses the component sensitivity threshold 1012 at peaks 1021-1023. The end 1024 of the AO window 1008 may be set to correspond to (or follow) the last intercept 1022 which crosses the threshold 1012 before the amplitude of the CA signal is reduced and no longer crosses the threshold 1012 or simply the max peak location+x % (PAVP−peak location). Optionally, an AP blanking interval 1030 may be provided to precede the PAVP window 1032 following a paced event. When an intrinsic atrial event is detected, the AP blanking interval 1030 may be omitted.

Figure 11:
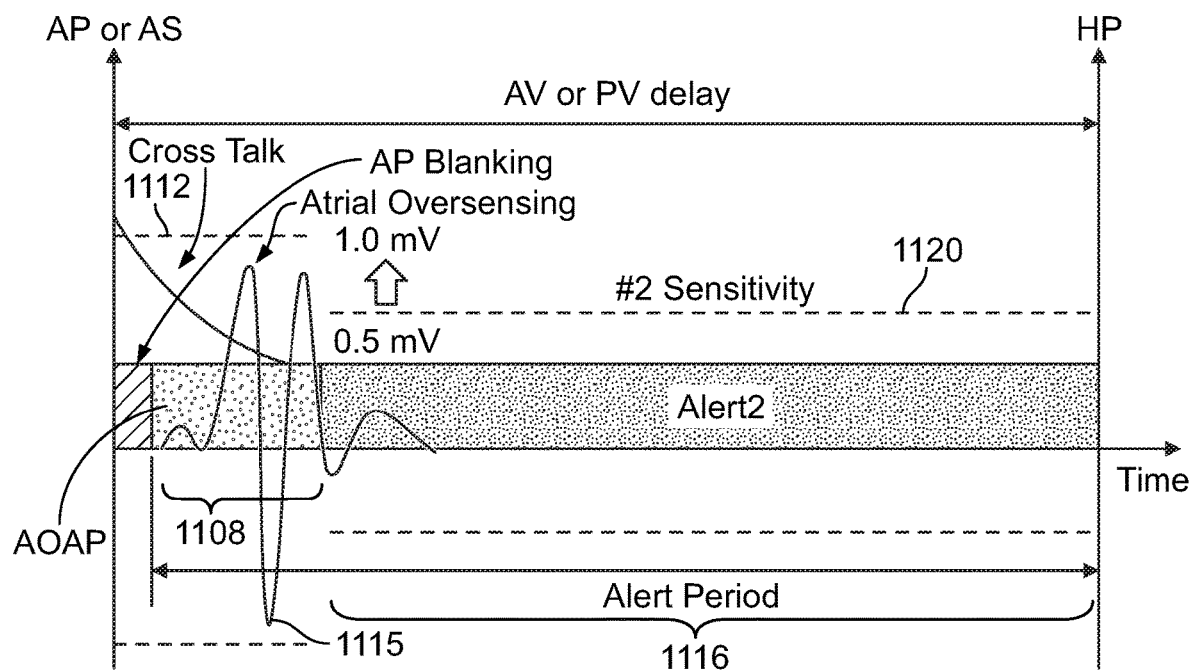
FIG. 11 illustrates an example in which different sensitivities are utilized during the AOA window and the alert window in accordance with embodiments herein.

Methods described in FIGS. 9 and 10 are for setting up AOA parameters for HBP that are needed in FIG. 11. In both methods, tests can run for number of beats over one or more respiration cycles for determination of AOA parameters. During the tests, AH delay can be set long enough such as >AVs or intrinsic AH. Alternatively, the tests can be done beat to beat in a parallel or serial manner to HBP in FIG. 11.

As noted herein, the sensitivity utilized during the PAVP window, AOA window and alert window may differ or be the same. FIG. 11 illustrates an example in which different sensitivities are utilized during the AOA window and the alert window. In FIG. 11, a component sensitivity threshold 1112 may be utilized during the AOA window 1108, while a VE sensitivity threshold 1120 is utilized during the alert window 1116. The transition from the sensitivity during the AOA to the VE sensitivity can have various profiles such as an angled straight line, tapered exponential decay etc. The sensitivity during the AOA window may be determined in various manners. For example, the process may identify a prior peak amplitude 1115 of the CA signal. During the next or subsequent beats, the process may set the component sensitivity threshold to be a predetermined amount higher than the last peak amplitude 1115. The VE sensitivity threshold 1120 may be maintained at a previously programmed level following the end of the AOA window 1108.

Optionally, the operations of FIG. 10 and FIG. 11 may be implemented in a sequential manner or a parallel manner.

Figure 12A:
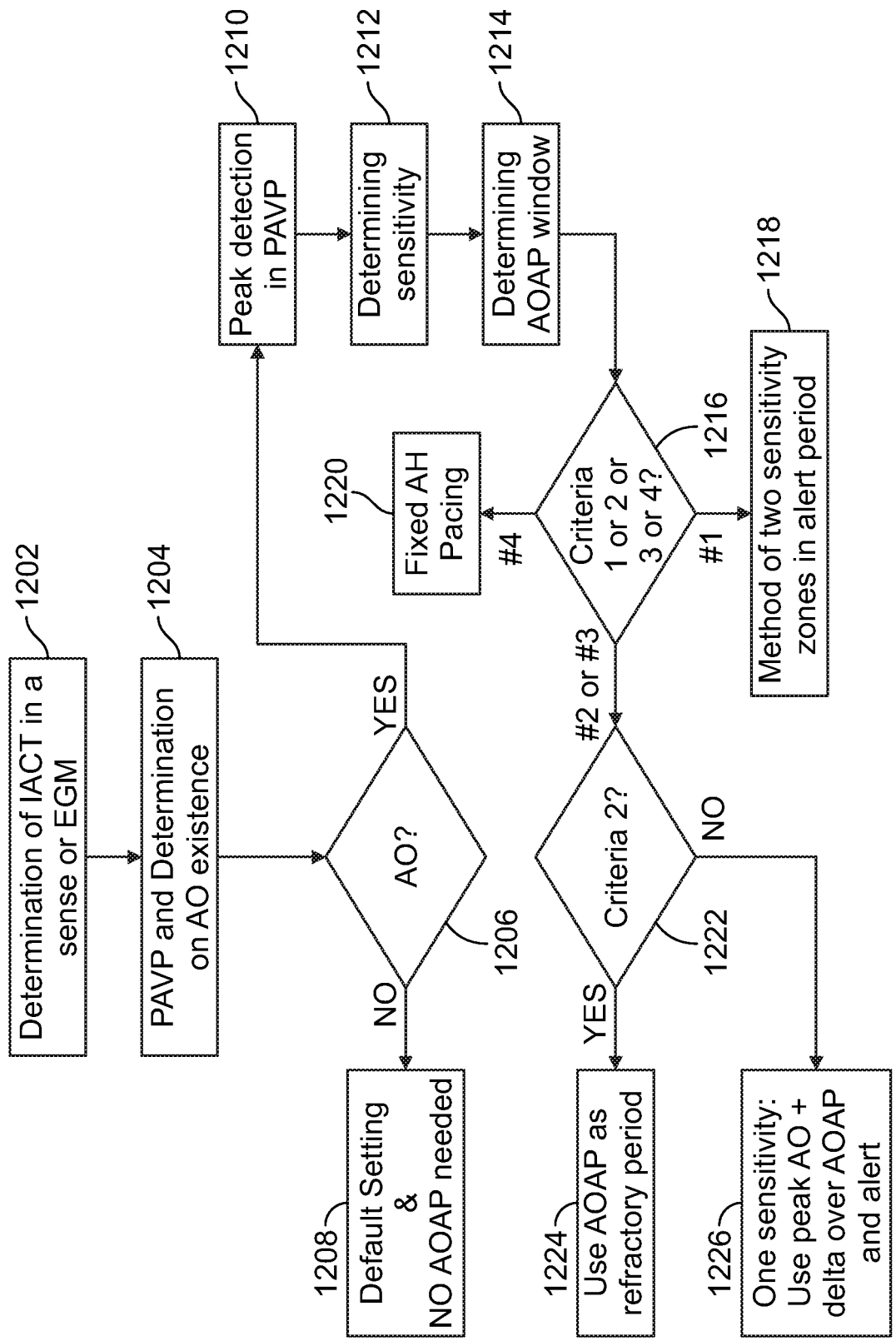
FIG. 12A illustrates a method for managing a sensing operation in connection with HIS bundle pacing in accordance with an alternative embodiment in accordance with embodiments herein.

FIG. 12A illustrates a method for managing a sensing operation in connection with HIS bundle pacing in accordance with an alternative embodiment. At 1202, one or more processors obtain CA signals over an atrial sensing channel. At 1202, the one or more processors determine an intrinsic IACD from the CA signals sensed over the atrial sensing channel. At 1204, the one or more processors utilize the PAVP window to monitor CA signals sensed over the HIS sensing channel 1204 to determine whether atrial oversensing is occurring after the atrial sensed or paced event on the atrial sensing channel. At 1206, when the one or more processors determined that no atrial oversensing occurs, flow moves to 1208. At 1208, the one or more processors use default settings and no AOA window is needed. Alternatively, at 1206, when the one or more processors determined that atrial oversensing is occurring, flow moves to 1210.

At 1210, the PAVP window is set based on the P-wave duration. At 1212, a sensitivity is determined for the PAVP window and/or AOA window based on the various embodiments described herein. At 1214, the duration of the AOA window is determined based on the various embodiments described herein. At 1216, the one or more processors determine which criteria apply to the present collection of CA signals. The process may utilize different sensitivity thresholds based on various criteria (referred to here as criteria 1-4). For example, criteria 1 may represent the situation in which a) the max peak of the AA component detected during the AOA window is larger than max peak of the VE components in the CA signal sensed over the HIS sensing channel, and b) the AOA window has a duration that is shorter than the programmed AH delay. When criteria 1 exists, flow moves to 1218, where the two sensitivity thresholds approach may be utilized.

Criteria 4 represents the situation in which a) the duration of the AOA window is close to or greater than the duration of the programmed AH delay and b) the max peak of the AA component has an amplitude close to or greater than max peak of the VE component. When criteria 4 exists, flow moves to 1220. At 1220, the one or more processors initiate a predetermined HIS bundle pacing mode in which the atrium and ventricle are continuously paced with a predetermined delay there between.

At 1222, the one or more processors determine whether criteria 2 or 3 exist. Criteria 2 represents the situation in which the max peak of the AA component detected during the AOA window has an amplitude that is close to or greater than max peak of a VE component in the CA signal sensed over the HIS sensing channel, and AOAP is shorter than programmed AH. When criteria 2 occurs, flow moves to 1224. At 1224, the one or more processors utilize the AOA window as the refractory period.

Criteria 3 represents the situation in which the duration of the AOA window is close to a programmed duration of the AH delay, but the peak of the AA component is lower than the max peak of the VE component in the CA signal and the difference reaches a criteria. When criteria 3 occurs, flow moves to 1226. At 1226, the one or more processors utilize a common sensitivity level for both the AOA window and the alert window.

Optionally, the Criteria 2&3 may be omitted and instead merged with the criterial 1 and 4.

The operations of the methods described herein may be implemented entirely or in part by one or more processors and/or circuitry of an implantable medical device. Optionally, certain operations of FIG. 6 may be implemented by one or more processors of a local external device, clinician programmer and/or remote server and then uploaded to an implantable medical device which in turn implements the remaining operations of FIG. 6. For example, the obtaining, identifying and calculating operations may be performed by a local external device, implantable medical device, clinician programmer and/or remote server prior to, during or after implant of an IMD, while the IMD then performs the remaining operations. It is recognized that additional and alternative combinations of the operations may be distributed between one or more external devices and the IMD.

In at least some of the processes described herein for detecting atrial oversensing and managing sensitivity utilizes an automated dynamic algorithm that collects various types of information over a desired number of beats before adjusting the VE sensitivity profile. For example, at least in connection with the embodiment of FIGS. 8-12, CA signals are collected for a desired number of beats before determining a max peak of the atrial oversensing signal and a length of the AOA window, and safety margin for them. While collecting the CA signals for the desired number of beats, the IMD may be placed in a pacing mode in which HIS bundle pacing is inhibited (e.g., inhibited for three-five beats). Additionally or alternatively, other types of sensors, such as an accelerometer, may be utilized to detect posture and activity changes to determine which beats should be utilized for collecting CA signals.

Figure 12B:
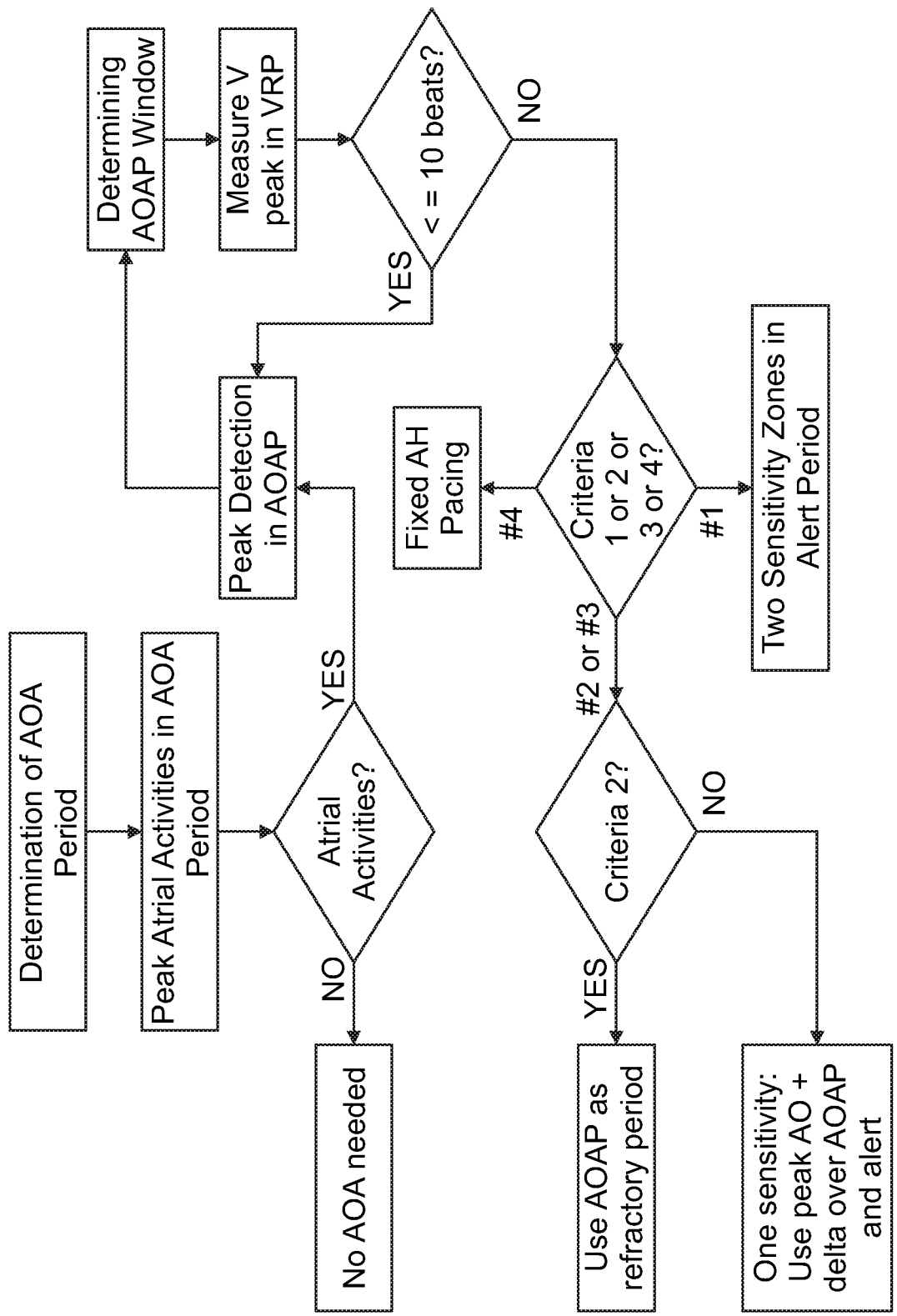
FIG. 12B illustrates a method for managing a sensing operation in connection with HIS bundle pacing in accordance with an alternative embodiment in accordance with embodiments herein.

FIG. 12B illustrates a method for managing a sensing operation in connection with HIS bundle pacing in accordance with an alternative embodiment. The operations if FIG. 12B are similar to the operations of FIG. 12A, but for the addition of a loop for measurements over a number of beats (e.g., 10 beats). In addition, the operations of FIG. 12B measure and utilize a Vpeak.

Figure 13:
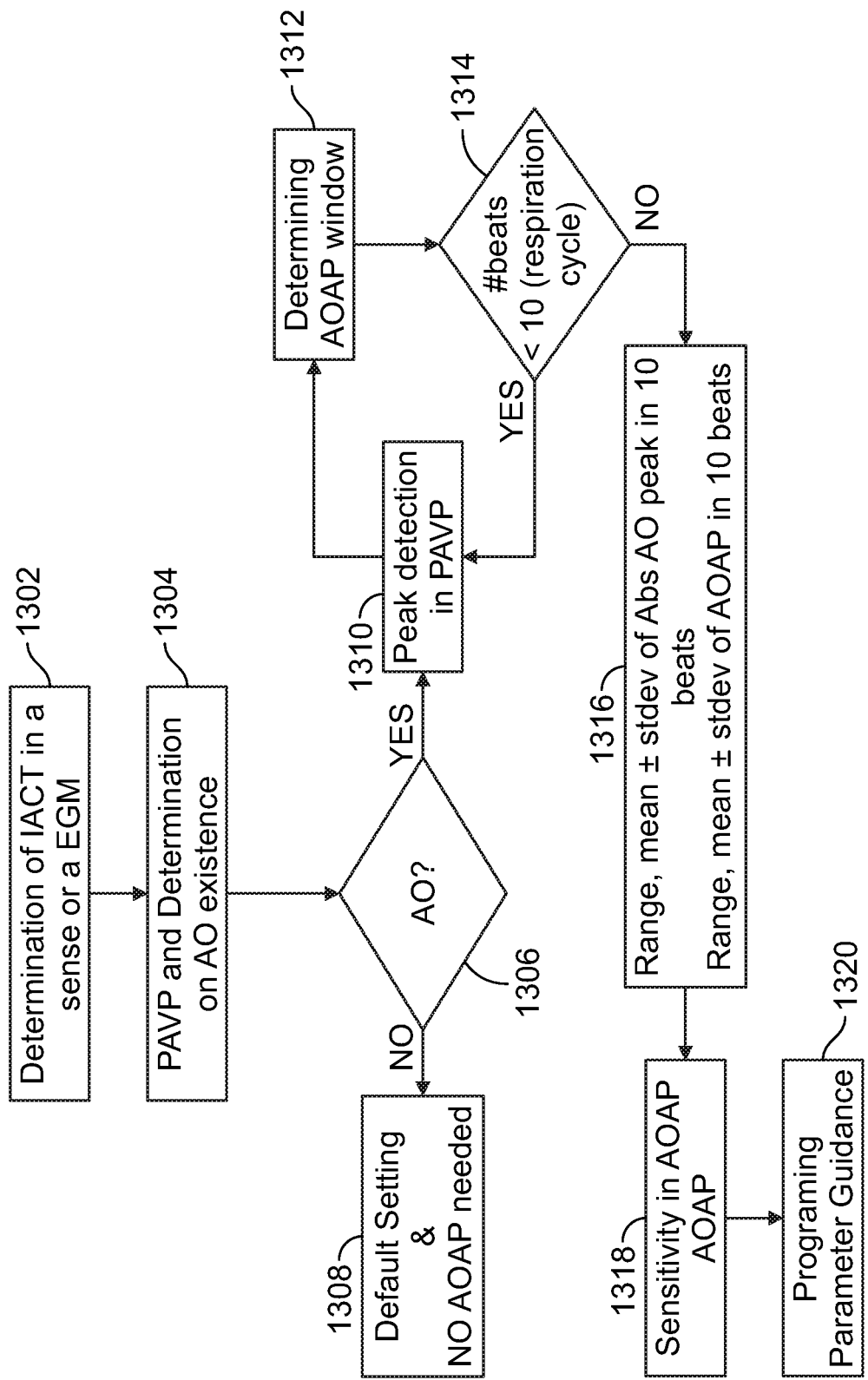
FIG. 13 illustrates a method for managing a sensing operation in connection with HIS bundle pacing in accordance with embodiments herein.

FIG. 13 illustrates a method for managing a sensing operation in connection with HIS bundle pacing in accordance with an alternative embodiment. At 1302, one or more processors obtain CA signals over an atrial sensing channel. At 1302, the one or more processors determine an intrinsic IACD from the CA signals sensed over the atrial sensing channel. At 1304, the one or more processors seta PAVP window to monitor CA signals sensed over the HIS sensing channel 1304 to determine whether atrial over sensing is occurring after the atrial sensed or paced event on the atrial sensing channel. At 1306, when the one or more processors determined that no atrial oversensing occurs, flow moves to 1308. At 1308, the one or more processors use default settings and no AOA window is needed. Alternatively, at 1306, when the one or more processors determined that atrial oversensing is occurring, flow moves to 1310.

At 1310, the one or more processors detect max peaks of the CA signals during the PAVP window for each beat. At 1312, the duration of the AOA window is determined. As one nonlimiting example, the duration of the AOA window may be defined based on the last intercepts of AA component to the threshold set slightly below the sensitivity threshold utilized during the PAVP window. At 1314, the one or more processors determine whether CA signals have been collected for a desired number of beats. For example, the desired number of beats may be the number of beats during one or more normal respiration cycle(s) and/or a predetermined number of beats (e.g., 8 or 10 enough over one respiration). When CA signals have not yet been collected for the desired number of beats, flow returns to 1312 for another cardiac cycle. When CA signals have been collected for the desired number of beats, flow moves to 1316.

At 1316, the one or more processors form a mathematical combination of the max peaks detected during the PAVP window for each beat and the different lengths determined for the AOA window. For example, the one or more processors may determine a range, mean, and/or standard deviation of the absolute value of the max peaks of the AA components in each beat over the predetermined number of beats. As a further example, the one or more processors may determine the range, mean and/or standard deviation of the lengths for the AOA windows across the predetermined number of beats. At 1318, the one or more processors utilize the mathematical combinations of the peaks and/or AOA window duration to set a sensitivity for the AOA window. At 1320, the one or more processors determine one or more parameters as described herein. For example, at 1320, the one or more processors determine the VE sensitivity profile to be utilized during the alert window.

Figure 14:
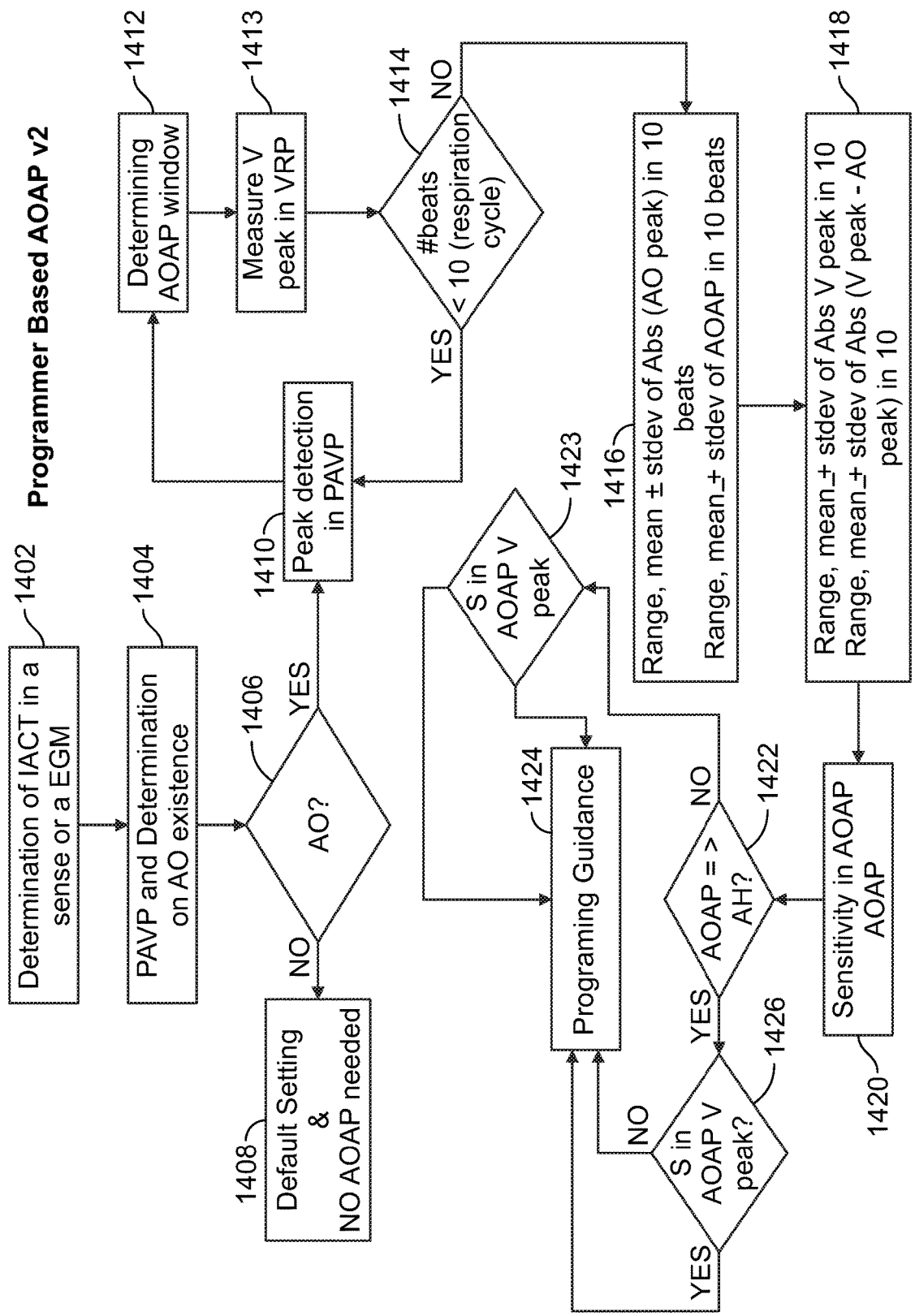
FIG. 14 illustrates a method for managing a sensing operation in connection with HIS bundle pacing in accordance with embodiments herein.

FIG. 14 illustrates a method for managing a sensing operation in connection with HIS bundle pacing in accordance with an alternative embodiment. At 1402, one or more processors obtain CA signals over an atrial sensing channel. At 1402, the one or more processors determine an intrinsic IACD from the CA signals sensed over the atrial sensing channel. At 1404, the one or more processors utilize the PAVP window to monitor CA signals sensed over the HIS sensing channel 1404 to determine whether atrial over sensing is occurring after the atrial sensed or paced event. At 1406, when the one or more processors determined that no atrial oversensing occurs, flow moves to 1408. At 1408, the one or more processors use default settings and no AOA window is needed. Alternatively, at 1406, when the one or more processors determined that atrial oversensing is occurring, flow moves to 1410.

At 1410, the one or more processors detect the max peaks of the CA signals during the PAVP window for each beat. At 1412, the duration of the AOA window is determined. As one nonlimiting example, the duration of the AOA window may be defined based on the last intercept of AA component to exceed the sensitivity threshold utilized during the PAVP window. At 1413, the one or more processors measure a max ventricular peak during the ventricular refractory period. At 1414, the one or more processors determine whether CA signals have been collected for a desired number of beats. For example, the desired number of beats may be the number of beats during a normal respiration cycle and/or a predetermined number of beats (e.g., 10). When CA signals have not yet been collected for the desired number of beats, flow returns to 1412 for another cardiac cycle. When CA signals have been collected for the desired number of beats, flow moves to 1416.

At 1416, the one or more processors form a mathematical combination of the peaks detected during the PAVP window, and the different lengths determined for the AOA window. For example, the one or more processors may determine a range, mean, and/or standard deviation of the absolute value of the peaks of the AA components over the predetermined number of beats. As a further example, the one or more processors may determine the range, mean and/or standard deviation of the lengths for the AOA windows across the predetermined number of beats.

At 1418, the one or more processors calculate mathematical combinations of the ventricular peaks and the AA component peaks. For example, the one or more processors determine a range, mean and standard deviation of the absolute value of the ventricular peaks over the predetermined number of beats. The further example, the one or more processors determine a range, mean and standard deviation of the absolute value of differences between the ventricular peaks and AA component peaks (e.g., abs($V_{peak}$−AA component$_{peak}$) over the predetermined number of beats.

At 1420, the one or more processors calculate AOA window length and sensitivity thresholds from the range, mean, and/or standard deviation obtained from 1416. Flow moves to 1422, where the one or more processors compare AOA window length to a programmed AH delay. If the AOA window length is equal to or greater than the programmed AH delay, flow moves to 1426; otherwise flow moves to 1422. At 1426 and 1423, the one or more processors compare a sensitivity threshold to the ventricular peak value.

At 1426, the one or more processors determine whether the sensitivity threshold is less than the ventricular peak value at 1423, the one or more processors determine whether the sensitivity threshold is less than the ventricular peak value. Next, flow moves to 1424, where the one or more processors provide the results of the corresponding determinations in connection with programming guidance. At 1424, the one or more processors program parameters for HIS pacing based on the conditions and inputs from 1422, 1423 and 1426.

Figure 15:
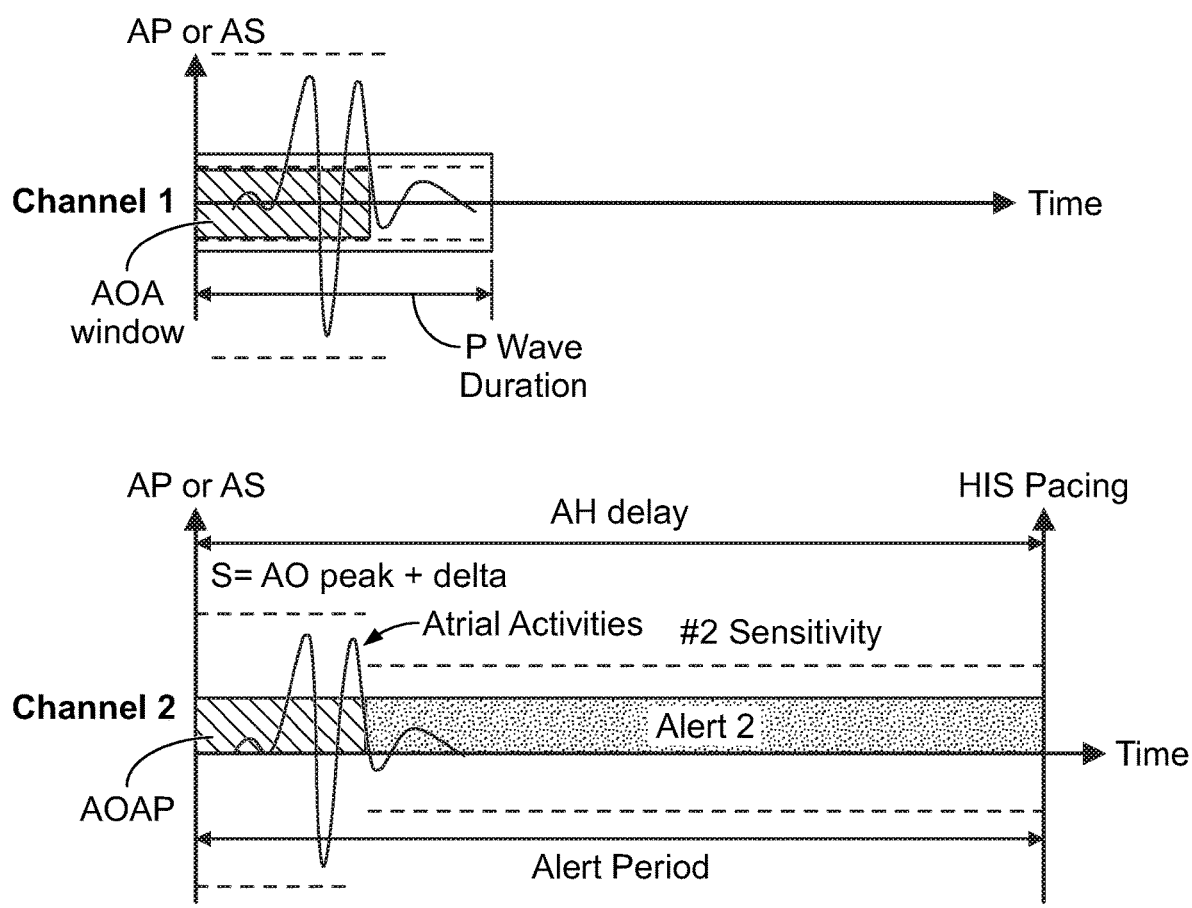
FIG. 15 illustrates a method for managing a sensing operation in connection with HIS bundle pacing in accordance with an alternative embodiment.

FIG. 15 illustrates a method for managing a sensing operation in connection with HIS bundle pacing in accordance with an alternative embodiment. The method utilizes two sensing channels (channel 1 and channel 2) connected to the HIS lead. A first channel (channel 1) is used for initiation of the AOA window and the sensitivity setting in connection with the AOA window. It also stores the parameters used in channel 2 for comparisons, such as Peak_AO and AOA window and they are over-written every time channel 2 has an updated parameter. If the difference in Peak_AO and/or AOA between channel 1 and channel 2 is greater than a threshold (e.g. 0.2 mV or 20 ms respectively), sensitivity thresholds in channel 2 will be updated. Optionally in channel 2, a sensitivity can be set just above the noise level such as 0.1 mV for detecting the first intercept and start the time search window. Alternatively, if channel 1 does not need to run continuously, channel 1 can be turned on or off triggered by the criteria. For example, if 1-3 HIS pacing beats are inhibited in channel 2, channel 1 can be turned on again or re-evaluation triggered by other sensors or predetermined period. Two channels can have different dynamic ranges. For example, channel 1 for atrial activities can have smaller dynamic ranges similar to RA channel (2-3 mV), while channel 2 can have dynamic range for ventricular signals (e.g. 10 mV).

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The nonsignal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. A method for pacing a HIS bundle of a patient heart using an implantable medical device (IMD), the method comprising:
   obtaining cardiac activity (CA) signals over a HIS sensing channel, the HIS sensing channel utilizing a HIS electrode;
   identifying at least one of a P-wave duration (PWD), an intrinsic atrial-HIS (AH) delay, or an intrinsic atrial conduction delay (IACD);
   calculating an atrial oversensing avoidance (AOA) window based on at least one of the PWD, AH delay or IACD;
   analyzing the CA signals, obtained over the HIS sensing channel during the AOA window, for an atrial activity (AA) component;
   based on the analyzing operation, adjusting a ventricular event (VE) sensitivity profile utilized by the HIS sensing channel;
   monitoring the CA signals, obtained over the HIS sensing channel during an alert window based on the VE sensitivity profile, for a ventricular component indicative of a ventricular event; and
   managing HIS bundle pacing based on the ventricular event, wherein the AOA window precedes a HIS paced event or intrinsic ventricular event.

2. The method of claim 1, wherein the calculating operation further comprises setting the AOA window to equal at least one of:
   a. the PWD when a difference between the AH delay and the PWD is greater than or equal to an alert minimum threshold; or
   b. a percentage of the PWD.

3. The method of claim 1, further comprising obtaining a second group of the CA signals over a right atrial (RA) sensing channel, a left ventricular (LV) sensing channel and/or electrocardiogram (ECG) sensing channel, the identifying including identifying at least one of the PWD or IACD based on the second group of the CA signals.

4. The method of claim 1, wherein the adjusting operation lowers a sensitivity level of the VE sensitivity profile for the HIS sensing channel.

5. The method of claim 1, further comprising maintaining a count of a number of AA components over a series of beats and, based on the count, determining whether to maintain or change current settings for a length of the AOA window and/or the VE sensitivity profile.

6. The method of claim 1, wherein the AOA window represents a time window enclosing atrial activity components.

7. The method of claim 1, wherein the calculating operation calculates a first AOA window, the method further comprising providing a second AOA window, that extends continuous with the first AOA window, the analyzing operation further comprising analyzing the CA signals during the first and second AOA windows.

8. The method of claim 7, wherein the first and second AOA windows have at least one of different durations or sensitivities.

9. The method of claim 1, wherein the analyzing operation is performed over a number of cardiac beats, from which one or more characteristics of interest from the AA component are mathematically combined and utilized to adjust the VE sensitivity profile.

10. The method of claim 9, wherein the analyzing operation is performed in a beat or a few beats over one or more respiration cycles in one channel connected to the HIS lead, from which comparisons to programming settings of the VE sensitivity profile in the other channel(s) also connected to the HIS lead for HIS pacing and adjustments of the VE sensitivity profile when criteria are met.

11. The method of claim 9, wherein the analyzing operation is performed in one beat, from which comparisons to programming settings of the VE sensitivity profile in the other channel(s) also connected to the HIS lead for HIS pacing to decide adjustments when criteria are met.

12. The method of claim 1, further comprising defining a post atrial ventricular period (PAVP) window, identifying peaks in the CA signal that exceed a PAVP sensitivity threshold utilized during the PAVP window, and defining a length of the AOA window based on a timing of a last one of the peaks in the CA signals during the PAVP window that exceed the PAVP sensitivity threshold.

13. The method of claim 1, wherein the calculating comprises calculating the AOA window based on at least one of the PWD or the AH delay.

14. A system, comprising:
a HIS electrode configured to be located proximate to a HIS bundle and to at least partially define a HIS sensing channel;
memory to store cardiac activity (CA) signals obtained over the HIS sensing channel, the memory to store program instructions; and
one or more processors that, when executing the program instructions, are configured for:
identifying at least one of a P-wave duration (PWD), an intrinsic atrial-HIS (AH) delay, or an intrinsic atrial conduction delay (IACD);
calculating an atrial oversensing avoidance (AOA) window based on at least one of the PWD, AH delay, or IACD;
analyzing the CA signals, obtained over the HIS sensing channel during the AOA window, for an atrial activity (AA) component;
based on the analyzing operation, adjusting a ventricular event (VE) sensitivity profile utilized by the HIS sensing channel;
monitoring the CA signals, obtained over the HIS sensing channel during an alert window based on the VE sensitivity profile, for a ventricular component indicative of a ventricular event; and
managing HIS bundle pacing based on the ventricular event, wherein the AOA window precedes a HIS paced event or intrinsic ventricular event.

15. The system of claim 14, wherein the one or more processors are further configured to set the AOA window to equal at least one of:
a. the PWD when a difference between the AH delay and the PWD is greater than or equal to an alert minimum threshold; or
b. a percentage of the PWD.

16. The system of claim 14, wherein the calculating operation, by the one or more processors, further comprises to set first and second AOA windows that extend continuous with one another following an atrial event, the first AOA window having a length corresponding to at least one of a predetermined time interval or a percentage of the PWD, the second AOA window having a length corresponding to at least one of a percentage of the PWD or the IACD.

17. The system of claim 14, wherein the adjusting operation lowers a sensitivity level of the VE sensitivity profile for the HIS sensing channel.

18. The system of claim 14, wherein the one or more processors are further configured to maintain a count of a number of AA component over a series of beats and, based on the count, determining whether to maintain or change current settings for a length of the AOA window and/or the VE sensitivity profile.

19. The system of claim 14, wherein the AOA window represents a post atrial ventricular period (PAVP) window.

20. The system of claim 14, further comprising an implantable medical device having a housing that includes the memory and the one or more processors, the housing configured to be coupled to an RA electrode and the HIS electrode.

21. The system of claim 14, further comprising an implantable medical device (IMD) having at least a portion of the one or more processors and an external device having at least a portion of the one or more processors, the IMD and external device both performing at least a portion of the identifying, calculating, analyzing, adjusting, monitoring and managing operations.

22. The system of claim 14, wherein the one or more processors are configured to perform the analyzing operation over a number of cardiac beats, from which one or more characteristics of interest from the AA components are mathematically combined and utilized to adjust the VE sensitivity profile.

23. The system of claim 14, wherein the one or more processors are further configured to define a post atrial ventricular period (PAVP) window, identify a maximum peak in the CA signal in the PAVP window, and define a length of the AOA window based on a timing of a last intercept of the CA signals during the PAVP window to a threshold set equal to or lower than a VE sensitivity threshold in alert period or based on a peak location and PAVP window size.

24. The system of claim 14, wherein the calculating comprises calculating the AOA window based on at least one of the PWD or the AH delay.

* * * * *